(12) United States Patent
Neuberger et al.

(10) Patent No.: US 7,271,187 B2
(45) Date of Patent: Sep. 18, 2007

(54) COMPOSITIONS AND METHODS FOR PROMOTING TISSUE REGENERATION

(75) Inventors: Timothy J Neuberger, Dobbs Ferry, NY (US); Uri Herzberg, 56 Horseshoe Rd., Guilford, CT (US) 06437; Veronica Mallon, 395 No. Little Tor Rd., New City, NY (US) 10956

(73) Assignees: Tim Neuberger, San Diego, CA (US); Uri Herzberg, Bridgewater, NJ (US); Veronica Mallon, New City, NY (US)

( * ) Notice: Subject to any disclaimer, the term of this patent is extended or adjusted under 35 U.S.C. 154(b) by 376 days.

(21) Appl. No.: 09/827,666

(22) Filed: Apr. 6, 2001

(65) Prior Publication Data

US 2002/0055530 A1     May 9, 2002

Related U.S. Application Data

(60) Provisional application No. 60/195,516, filed on Apr. 6, 2000.

(51) Int. Cl.
    *A61K 31/41*     (2006.01)
    *A61K 31/4188*     (2006.01)
    *A61K 31/4178*     (2006.01)

(52) U.S. Cl. .................. 514/381; 514/382; 514/393; 514/396; 514/397

(58) Field of Classification Search ................ 514/433, 514/605, 318, 381, 382, 396, 397, 437, 438; 435/353, 354, 368
See application file for complete search history.

(56) References Cited

U.S. PATENT DOCUMENTS 5,959,107 A     9/1999     Ishiguro et al.

OTHER PUBLICATIONS

"Beyond Animal Research", Kristie Stoick, 2005, www.pcrm.org.*
"Gene Therapy for neurodegenerative diseases: fact or fiction?", Carter et al., 2001, British Journal of Psychiatry, 178, 392-394.*
"Animal Models of Spinal Cord Injury", Stephen K Kaufman, M.D., Perspectives on Medical Research, vol. 2, 1990.*

* cited by examiner

*Primary Examiner*—Brian Kwon

(57) ABSTRACT

The present invention relates to compositions and methods for promoting tissue regeneration, preferably neural tissue regeneration. Compositions of the invention include (i) certain diphenyl sulfides, diphenyl sulfoxides, diphenyl sulfones, and sulfide, sulfoxide and sulfones of dibenzothiophene and thioxanthene, as well as various analogues and derivatives of these compounds; (ii) one or more cells harvested from an animal or organism subsequent to the administration of a composition comprising a compound of (i); or (iii) any combination of (i) and (ii). The invention can be useful in treating decreases in neuronal function, for example from injury or disease.

1 Claim, No Drawings

COMPOSITIONS AND METHODS FOR PROMOTING TISSUE REGENERATION

This application claims benefit of 60/195,516 filed Apr. 6, 2000.

The present invention relates to promoting tissue regeneration, such as neural tissue or liver tissue regeneration. More specifically, the present invention employs (i) certain diphenyl sulfides, diphenyl sulfoxides, diphenyl sulfones, and sulfide, sulfoxide and sulfones of dibenzothiophene and thioxanthene, The nervous system consists essentially of two categories of cells, neurons and glial cells. During neuronal development, immature nerve cell bodies migrate along glial cells to a location in the brain, where neurite processes (dendrites and axons) grow out from the nerve cell body. A growth cone at the tip of each process guides the path taken by each process, determining the path of neuron growth. A number of factors influence the path of neuron growth, including nerve growth factor (NGF) and local contact with cell-cell adhesion molecules, contact with extracellular matrix molecules and various other forms of chemotactic guidance. Cell-cell adhesion molecules that influence neuron growth include membrane glycoproteins such as members of the immunoglobin superfamily which includes Neural Cell Adhesion Molecule (NCAM), and the $Ca^{2+}$ dependent cadherin family of proteins (N-cadherin). Extracellular matrix proteins involved in guiding nerve cell growth include laminin, to which growth cones can bind at integrin receptors.

During development of the central nervous system ("CNS"), multipotent precursor cells, also known as neural stem cells, proliferate, giving rise to transiently dividing progenitor cells that eventually differentiate into the cell types that compose the adult brain. Neural stem cells are classically defined as having the ability to self-renew (i.e., form more stem cells), to proliferate, and to differentiate into multiple different phenotypic lineages, including neurons and glial cells (glia), such as astrocytes and oligodendrocytes. These neural stem cells have been isolated from several mammalian species, including mice, rats, pigs and humans. See, e.g., WO 93/01275, WO 94/09119, WO 94/10292, WO 94/16718 and Cattaneo et al., Mol. Brain Res., 42, pp. 161-66 (1996). Human CNS neural stem cells, like their rodent homologues, when maintained in a mitogen-containing (for example, epidermal growth factor or epidermal growth factor plus basic fibroblast growth factor), serum-free culture medium, grow in suspension culture. See, e.g., Cattaneo et al., *Mol. Brain Res.,* 42, pp. 161-66 (1996). Upon removal of the mitogen(s) and provision of a substrate, the stem cells differentiate into neurons, astrocytes and oligodendrocytes.

Just how many different kinds of precursor cells there are in the developing brain is unknown. However, several distinct cell types can exist, such as precursors to neurons, oligodendrocytes and astrocytes. Fate mapping analysis and transplantation studies in vivo have shown that different neuronal types and non-neuronal cells can be derived from the same precursor cells (See Turner, D. L. & Cepko, C. L., *Nature* 328, 131-136 (1987); Gray, G., Glover, J., Majors, J. & Sanes, J., *Proc. Natl. Acad. Sci. USA* 85, 7356-7360 (1988); Wetts, R. & Fraser, S., *Science* 239, 1142-1145 (1988); McConnell, S., *Curr. Opin. Neurobiol.* 2, 23-27 (1992); and Walsh, C. & Cepko, C. L., *Nature* 362, 632-635 (1993)). In vitro analyses have also suggested that multipotential cells are present in the developing brain (See Davis, A. A. & Temple, S., *Nature* 372, 263-266 (1994); and Williams, B. & Price, J., *Neuron* 14, 1181-1188 (1995)). Lineage analysis alone, however, does not directly identify the multipotential cells; nor does it define the mechanisms that drive them to different fates. Precursor cells from the CNS have been expanded in vitro and differentiation into neurons and glia has been observed (See Cattaneo, E. & McKay, R. D. G., *Nature* 347, 762-765 (1990); Reynolds, B., Tetzlaff, W. & Weiss, S., *J. Neurosci.* 12, 4565-4574 (1992); Ray, J., Peterson, D., Schinstine, M. & Gage, F., *Proc. Natl. Acad. Sci. USA* 90, 3602-3606 (1993); Ghosh, A. & Greenberg, M., *Neuron* 15, 89-103 (1995); and Vicario-Abejon, C., Johe, K., Hazel, T., Collazo, D. & McKay, R., *Neuron* 15, 105-114 (1995)) and markedly different cell types have been obtained even when the culture conditions used were seemingly the same. The entire subject of the isolation, characterization, and use of stem cells from the CNS has been reviewed (See Svendsen, C. N. & Rosser, A. E., *Trends in Neuroscience* 18, 465-466 (1995); Gage, F. H., Ray, J. & Fisher, L. J., *Annu. Rev. Neurosci.* 18, 159-192 (1995); and Kilpatrick, T. J., Richards, L. J., and Bartlett, P. F., *Mol. Cell. Neurosci.* 6, 2-15 (1995)).

Once mature, nerve cells of the central nervous system, which includes the brain and spinal cord, or "neurons," consist of a cell body (the "soma") and an "axon" projecting from the cell body through which nerve impulses travel. The cytoskeleton of mature neurons is primarily made up of microtubules (also called neurotubules), neurofilaments and microfilaments, as well as several associated proteins. Microtubules are comprised of alpha-tubulin and beta-tubulin subunits. Neurofilaments are formed largely by three types of neurofilament proteins (NFPs) called neurofilament-light (NF-L), neurofilament-medium (NF-M) and neurofilament heavy (NF-H) which have molecular weights of 68, 160 and 200 kDa respectively. Microtubule-associated proteins (MAPs) and tau-proteins form cross-linking structures between microtubules and other cellular components. MAP-II (also called MAP2) is a major brain MAP that regulates the assembly and stability of neuronal microtubules, is a major site for the phosphorylation of cAMP-dependent protein kinase in neurons and is found in dendrites in the developing brain. MAP-II and beta-tubulin are strongly expressed in the soma and dendrites of normal neurons. Studies have found MAP-II mRNA localized only in grey matter, appearing in cerebral neurons only after they have stopped dividing and migrated to the cortical plate (Tucker, RP et al, *Neuron* March 1989; 2(3): 1245-1256). The downregulation of MAP-II is believed to be a sensitive marker for ischemia in neurons (Rosenstein, J M, Cell Transplant January-February 1995; 4(1): 83-91).

The differentiation and growth of precursor and progenitor cells in the mature CNS can be influenced by the chemical environment of these cells. Differentiation of precursor and progenitor cells has been observed in cells from the CNS. Glial progenitor cells can differentiate in vitro into either oligodendrocytes or astrocytes, depending on the biochemical environment. For instance, maturation of O-2A progenitors is known to be influenced be the presence of growth factors and extracellular matrix molecules (See Zajicek, J & Compston, A; *Brain*, December 1994, 117 (Pt 6): 1333-1350). Oligodendrocyte progenitor cells (OP) and totipotent neural stem cells are known to be present in the adult CNS of mammals (See Rogister, B et al, *Acta Neurol Belg* March 1999; 99(1) 32-39). O-2A progenitor cells, precursors of oligodendrocytes in the CNS, are believed to originate in the subventricular geminal zones of the developing CNS and subsequently migrate away from this region to the rest of the CNS where they form oligodendrocytes.

(See Collarini, E J et al, *J Cell Sci Suppl* 1991; 15: 117-123). Platelet-derived growth factor (PDGF) and basic fibroblast growth factor are believed to be play roles in the determining course of OA-2 progenitor cell differentiation and proliferation (See Collarini, E J et al, *J Cell Sci Suppl* 1991; 15: 117-123).

The differentiated CNS shows very limited regenerative growth in vivo after lesions. The brain is composed of highly diverse nerve cell types making specific interconnections and, once destroyed, the nerve cells (neurons) do not normally regenerate. Much of the adult central nervous system is unable to grow new neurons or generate new axons. Injuries to neurons involving transection of, or damage to, the axons (termed "axotomy") characteristically result in retrograde neuronal dysfunction or death to most of these cells. Such injuries can result, for example, from trauma to the head or spinal cord, or as a consequence of surgical procedures intended to correct certain conditions of the nervous system. In addition, damage to axons can occur as a result of neurodegenerative disease, excitotoxic injury, or chemotherapy or radiation therapy. Excitotoxic injury is produced when the concentration of an excitatory amino acid, such as glutamate, or of a compound which is an analogue that activates excitatory amino acid receptors (an "agonist"), becomes excessive in the brain or spinal cord. The amount of excitotoxins released increases in response to abnormal conditions (i.e., seizure, hypoglycemia, and the like) and results in neural loss in the areas of concentration. Excitotoxic injury is produced either by increased extracellular excitatory amino acids associated with pathological conditions (i.e., ischemia, epilepsy, and the like), or by the direct injection into the brain of an excitatory amino acid or specific analogue.

Current approaches for treating the loss of neural function that accompanies neuron cell death include the replacement of damaged or dead neural tissue with various transformed cells of neural and non-neural origins, neutralizing the nerve-growth inhibitory properties of various proteins in the CNS environment, as well as introduction of stem cells or progenitor cells.

One approach to regain a lost neural function can be to replace the damaged cells with healthy cells. This ideally requires cells of neuronal origin that (1) proliferate in culture to a large number, (2) are amenable to various methods of gene transfer, and (3) integrate and behave as the cells of a normal brain. While transplantation of nervous tissue to the spinal cord has been attempted on animals and has been shown to improve the regeneration after an injury, the functional recovery after such transplantation is often deceptive and improvement of this method is needed before it can be attempted on patients. Several models have been used, including intraspinal bridges, transplants of glial cells, bridges of peripheral nerves, or replacement of missing supra-spinal afferents (Privat, Neurosci. Lett., 66:61-66 (1986)).

Another approach to promoting the regeneration of CNS tissue involves studies aimed at neutralizing the nerve-growth inhibitory action of various components of the CNS environment. Regrowth of axons in peripheral nervous system (PNS) tissue suggests that the environment of the CNS, for example the presence of glial cells such as oligodentrocytes or astrocytes, can play a role in precluding in vivo nerve cell regeneration. While adult CNS axons do not usually regenerate in vivo, adult axons have been shown to regrow through grafts of PNS tissue (See David, D. and Aguayo, A. J., *Science* 214, 931 (1981)). Schwab et al. found that neurons in culture are capable of generating axons across PNS glial cells (i.e. Schwann cells), but not across CNS glial cells (i.e. oligodendrocytes and myelin) (See Schwab, M E & Thoenen, H M, *J. Neurosci* 5 (1985) 2415-2423; Schwab, M E & Caroni, P, J Neurosci 1 (1988) 2381-2393). Investigations have focused on discovering components of CNS tissue that can inhibit axon regeneration. A number of proteins have been identified in myelin and oligodendrocytes that inhibit axon regeneration or nerve growth (See, for example, WO98/22499). Research by Schwab et al. focused on developing antibodies to these proteins lead to the discovery of the IN-1 antibody and showed the IN-1 antibody to allow for in vitro growth of nerve cells on usually inhibitory CNS tissue substrates, such as oligodentrocytes and myelin (See Caroni, P & Schwab, M E, Neuron 1 85 (1988) 96); in vivo investigations of IN-1 in treating spinal cord injuries in rats have shown 5% nerve regeneration (See Bregman, B S et al, *Nature* 378 (1995) 498-501). It is not known, however, whether this approach to overcoming the inhibitory properties of the CNS tissue environment will prove successful in ensuring functional nerve regeneration in vivo. For example, considering that neuron growth during development requires stimulation, for example by Nerve Growth Factor (NGF), it is not fully known whether stimulation of the regrowth of mature CNS neurons will be limited by compromised access of neurons to stimulatory mechanisms, in addition to inhibitory proteins in the CNS. Growth of most neurons requires specific signals (trophic factors) to reach their target cells and survive. Neuropathies in many diseases may be caused by or involve lack of such growth factors. Thus, it is not known whether neutralizing the inhibitory action of certain CNS proteins will adequately promote functional neural regeneration in vivo.

Clearly, there exists a need for treatments and compositions which will promote the regeneration of nerve cells in vivo. The compositions and methods of the present invention can promote regeneration of nerve cells through the differentiation and regeneration of nerve cells or glial cells, for example from progenitor cells. In some embodiments, the compositions and methods of the invention can stimulate endogenous populations of neural cells to expand and differentiate into neurons. Some methods of the invention allow for intrinsic stem cell stimulation after transplant of cells, as well as the potential for autologous transplantation. For example, autologous transplantation can be accomplished using the patient's own stem cells, or stem cells from another accompanied by appropriate pharmaceutical compositions and treatments. The genesis or growth of neurons, for example from progenitor cells, is often preceded by the upregulation of a variety of proteins. For example, embryonic NCAM (eNCAM) is widely but transiently expressed early in embryogenesis. Likewise, subsequent expression of beta-tubulin and MAP-II are also indicative of the expression of proteins involved in the genesis and growth of nerve cells. The appearance of phosphorylated neurofilament protein subsequent to beta-tubulin and MAP-II are also markers of the genesis and growth of neurons. The methods of the invention promote the differentiation or growth of neural progenitor cells by the administration of certain compositions which are described below.

There is an ongoing need to regenerate liver cells to overcome damage to the liver caused, for example, by injury, pathogens, chemicals, such as alcohol, drugs or toxins, inflammatory responses, auto immune disease and the like. The present inventors provide a method for regenerating liver cells.

SUMMARY OF THE INVENTION

The present invention provides, in some embodiments, a method for promoting tissue regeneration or tissue expression comprising administering to a mammal a tissue regeneration promoting effective amount or a tissue expression promoting effective amount of a composition containing a compound having one of the following structural formulas:

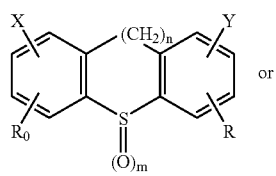
(I)

or

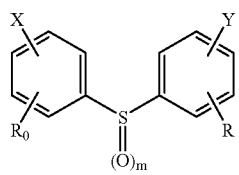
(II)

wherein n is 0 or 1; m is 0, or 2; X and Y are independently hydrogen or halogen, nitro, alkoxy or —NHCOCH$_2$NHCH$_3$; R and R$_0$ are independently H, halogen or a moiety of one of the following formulas:

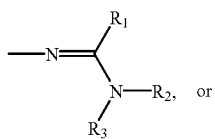
(Ia)

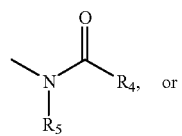
(Ib)

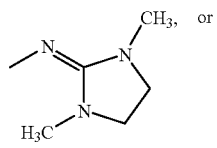
(Ic)

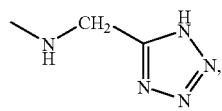
(Id)

or —N=CHOC$_2$H$_5$ or —(CH$_2$)$_q$CN where q is an integer from 1 to 5;

wherein R$_1$ is hydrogen, or linear or branched alkyl; cycloalkyl or aryl rings, which cycloalkyl or aryl rings can comprise one or more heteroatoms selected from O, N and S and which cycloalkyl or aryl rings can be substituted with linear or branched alkyl, halo, nitro or amino; or R$_1$ is a moiety of the formula:

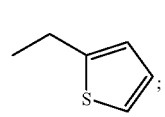
(Ie)

R$_2$ is hydrogen, alkyl or branched alkyl or benzyl;

R$_1$ and R$_2$ taken together may be —(CH$_2$)$_p$— where p is an integer from 2 to 4 and wherein R$_3$ is methyl;

R$_3$ is alkyl, branched alkyl, or cycloalkyl;

R$_4$ is linear or branched alkyl optionally substituted with 1 or more halogen, amino or alkylamino; or aryl optionally substituted with one or more alkyl, halo, nitro or amino moieties; —(CH$_2$)$_q$CN where q is an integer from 1 to 5, —CH$_2$COR$_6$ or —CH$_2$—NR$_7$R$_8$;

R$_2$ and R$_3$ taken together with the associated nitrogen can be pyrrolidino, piperidino, morpholino, thiomorpholino, 4-methylpiperazino, 3-azabicyclo[3.2.2]nonyl, azetidino or azaspiro[5,5]undecanoyl;

R$_5$ is hydrogen, alkyl or branched alkyl; and

R$_6$, R$_7$ and R$_8$ are independently hydrogen, or linear or branched alkyl optionally substituted with 1 or more halo, nitro or amino groups;

and pharmacologically acceptable salts thereof. In some embodiments, the compositions of the invention additionally comprise a pharmacologically acceptable carrier. Preferably the tissue is neural, liver, pancreatic or muscle, more preferably neural or liver, most preferably neural.

In some embodiments, the invention provides methods for promoting a tissue expression, or tissue regeneration, preferably, in each instance, neural, liver, pancreatic or muscle, more preferably neural or liver, most preferably neural, comprising administering to a first mammal a tissue expression promoting effective amount or a tissue regeneration in each instance, preferably neural, promoting effective amount of a composition, collecting cells from the first mammal and delivering them to a site of injury in the first mammal or in a second mammal; wherein the composition comprises a compound of Formula (I) or Formula (II) above. In some embodiments, the collected cells are bone marrow cells from an animal treated according to a method of the invention; in some embodiments, the cells are delivered to the site of injury in the first mammal. Preferably, the first mammal is human.

In some embodiments, the methods of the invention include administering to a mammal a tissue regeneration promoting effective amount or a tissue expression promoting effective amount, preferably the tissue is neural, liver, pancreatic or muscle, more preferably neural or liver, most preferably neural, of a composition containing a compound having one or more compounds of the following formula:

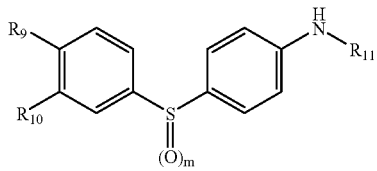
(III)

wherein m is 0, 1 or 2; $R_9$ is hydrogen, fluoro, chloro, bromo, nitro, alkoxy having up to 3 carbon atoms or —NHCOCH$_2$NHCH$_3$; $R_{10}$ is hydrogen or chloro; and $R_{11}$ is —(CH$_2$)$_q$CN wherein q is an integer from 1 to 5, —COCH$_2$NH$_2$, —COCH$_2$NHCH$_3$, —COCH$_2$Cl, —COCH$_2$CH$_2$Cl or —C(O)R$_{12}$ wherein $R_{12}$ is alkyl group having up to 4 carbon atoms such as methyl, isopropyl, n-butyl, and the like. In particularly preferred embodiments of the invention, methods are practiced using compositions comprising N-[4-[(4-fluorophenyl)sulfonyl]phenyl]acetamide. In some embodiments, the compositions of the invention additionally comprise a pharmacologically acceptable carrier.

In preferred embodiments of the invention, compositions or methods of the invention are effective to promote the expression of one or more proteins selected from the group consisting of: eNCAM, MAP II, beta-tubulin, nestin, NF and NF-PO$_4$; said protein expression preferably occurring in the bone marrow or neural tissue of the mammal.

The compositions and methods of the invention are effective to promote increased neural function, preferably recovery of neuronal function, after a decrease in neuronal function due to a trauma, an injury or a neurodegenerative disease or condition. In some embodiments, the decrease in neural function can be due to an injury to neural tissue as a result of surgery, acute or chronic spinal cord injury, radiation or chemical injury, such as injury caused by chemotherapy or radiation therapy. In some embodiments, the decrease in neural function can be due to a chemical injury caused by an excitotoxic agent such as glutamate, which can be released following head injury, stroke, epilepsy or spinal cord injury. In some embodiments, the decrease in neural function is due to a neurodegenerative condition or disease. Nonlimiting examples of neurodegenerative neurodegenerative diseases include: Alzheimer's disease (AD), Parkinsinson's Disease (PD), Huntington's Disease (HD) (also called Huntington chorea), HIV-1 infection, AIDS dementia, amyotrophic lateral sclerosis (ALS), spinal cerebellar degeneration, diabetes mellitus, senile dementia, dysplasia, stroke, trauma, hereditary hemorrhage with amyloidosis-Dutch type, cerebral amyloid angiopathy, Creutzfeld-Jakob disease, Parkinson's disease or multiple sclerosis (MS). In some embodiments, the decrease in neural function is due to spinal cord injury, including compression of the spinal cord.

In some embodiments, compositions or methods of the invention can treat a neurodegenerative condition or disease such as Parkinson's Disease, Alzheimer's disease, Huntington's Disease, HIV-1 infection, AIDS dementia, amyotrophic lateral sclerosis, stroke, trauma, hereditary hemorrhage with amyloidosis-Dutch type, cerebral amyloid angiopathy, Creutzfeld-Jakob disease or multiple sclerosis (MS). In some preferred embodiments, the compositions or methods of the invention can treat injury to neural tissue including traumatic injury, or injury to neural tissue resulting from surgery. In some preferred embodiments, the compositions or methods of the invention improve recovery of learning and memory function in a mammal, which untreated mammal has sustained a decrease in or a loss of neuronal function prior to the administration.

In some embodiments, the invention provides a composition adapted for parenteral, administration, preferably intrathecially or intralesionally, comprising a compound of Formula (I) or Formula (II) above, preferably compounds of Formula (II) that are described by Formula (III); which composition further comprises a parentally and pharmaceutically acceptable carrier.

In some embodiments, the invention provides a composition optionally adapted for parenteral administration, preferably intralesionally or intrathecial, comprising one or more cells obtained from a mammal subsequent to administration to the mammal of at least one compound of Formula (I) or Formula (II), preferably those compounds of Formula (II) that are also described by Formula (III), further optionally comprising a pharmaceutically acceptable carrier and wherein the composition can optionally contain a compound.

In some embodiments, the invention provides methods for promoting the proliferation or differentiation of progenitor cells comprising contacting the progenitor cells with a proliferation effective or differentiation effective amount of a composition of the invention, containing a compound of Formula (I) or Formula (II), preferably those compounds of Formula (II) that are also described by Formula (III).

In all methods of administration the compositions preferably includes a pharmaceutically acceptable carrier and generally preferably administered to a human.

The present invention also includes a method for promoting regeneration of cells comprising administering to a first mammal, so as to contact certain cells, a compound of formula (I) or (II), harvesting the resulting contacted cells, and administering the harvested cells to a second mammal, wherein the first mammal and the second mammal are the same or different and the second mammal is preferably a human.

Another aspect of the present invention is a method of treating a mammal, preferably a human having a liver disease or condition associated with a decrease in liver function or cellular death or dysfunction by administering an effective amount of a composition having formula (I) or (II). The disease or condition can be cirrhosis, noncirrhotic fibrosis, hepatitis associated with a toxin, drug or an infectious microorganism.

The invention includes a method of repairing a damaged liver by administering to a mammal, preferably a human, a liver repairing effective amount of a composition of formula (I) or (II).

Furthermore, the invention includes a method of growing cells, preferably liver cells, in vitro or in vivo by contacting the cells with a compound of formula (I) or (II).

The invention also includes a method for growth of liver cells in culture for use in transplants by removing the liver cells from a first patient, placing the cells in a medium supplemented with a compound of formula (I) and (II); incubating the cells to allow expansion of the cells, and transforming the cells to a second patient, wherein the first patent and the second patient can be the same or different.

Definitions

The following terms shall have, for the purposes of this application, the respective meaning set forth below:

"Alkyl" shall mean $C_1$-$C_6$ linear or branched alkyl groups.

"Alkoxy" shall mean linear or branched $C_1$-$C_6$ alkoxy groups, preferably $C_1$-$C_3$ alkoxy groups.

"Aryl" shall mean $C_5$-$C_{12}$ aryl groups optionally substituted with 1 or more heteroatoms selected from the group consisting of N, S and O; preferably, aryl includes $C_5$ or $C_6$ aryl groups which can include, but are not limited to, imidazole, thiazole, pyrazine, pyrimidine, pyrrole, furan, thiophene, pyridine or phenyl groups; most preferably, pyrrole, furan, thiophene, pyridine or phenyl groups.

"Cell regeneration" shall mean the growth or revitalization of an existing cell or the differentiation of progenitor cells into the desired cell.

"Cycloalkyl" shall mean $C_3$-$C_{12}$ cycloalkyl groups, optionally substituted with 1 or more heteroatoms selected from the group consisting of N, S and O; preferably $C_3$-$C_6$ alkyl groups including, but not limited to, ethylene oxido, azetidino, oxetano, thietano, tetrahydrofurano, pyrrolidino, piperidino, morpholino, oxazolidino, dioxano, dioxolano, tetrahydrothiopheno, cyclopentyl and cyclohexyl groups.

"Liver cell regeneration" shall mean the growth or revitalization of existing liver cells or the differentiation of progenitor cells into liver cells.

"Optionally substituted" shall mean substituted with between zero and a number of groups required for saturation of a particular moiety. For example, a "methyl group optionally substituted with halo atoms" would include a methyl group with 0, 1, 2 or 3 halogen atoms bonded to the carbon atom.

"Halogen" or "halo atom" shall mean chloro, fluoro, bromo or iodo moieties.

"Neural tissue" shall mean all tissue endogenous to the nervous system including without limitation neurons and glial cells (e.g., oligodendrocytes, myelin, astrocytes and Schwann Cells) and their progenitor cells.

"Neural expression promoting effective amount" shall mean an amount sufficient to induce a detectable increase in the expression of proteins indicative of neural tissue growth or neural tissue cell differentiation from progenitor cells, in a treated sample when compared to an untreated control sample. Nonlimiting examples of proteins indicative of nerve tissue growth or differentiation include: eNCAM, MAP, beta-tubulin, nestin, NGF receptor proteins and neurofilament proteins.

"Neural growth promoting effective amount" shall mean an amount sufficient to induce a detectable growth of neural tissue cells or neural tissue cell differentiation from progenitor cells, in a treated sample when compared to an untreated control sample.

"Neural regeneration" shall mean the growth or revitalization of existing mature neural tissue cells, the differentiation of progenitor cells into neural tissue cells, which progenitor cells can originate from neural tissue or non-neural tissue, or the increased expression of proteins indicative of neural tissue growth, neural tissue generation or progenitor cell differentiation into neural tissue cells.

"Neural precursor cell" shall mean any cell that is capable of differentiating directly into a neural tissue cell.

"Neural progenitor cell" shall mean any cell that can differentiate into a neural tissue cell, or be induced to differentiate into a neural tissue cell, including neural precursor cells, whether directly or through intermediate cell stages.

"Tissue" shall mean one or more cells of a particular type.

DETAILED DESCRIPTION OF THE INVENTION

The invention provides methods for promoting tissue cell replacement or growth comprising administering to an animal, preferably a mammal, more preferably a human, an expression-promoting effective amount, or a tissue growth-promoting effective amount, of a composition containing a compound according to any one of the following structural formulas:

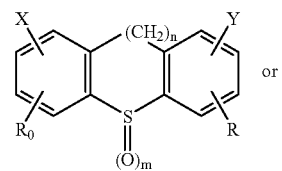

(I)

or

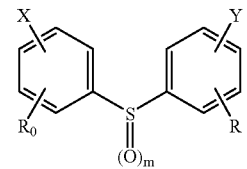

(II)

wherein n is 0 or 1; m is 0, or 2; X and Y are independently hydrogen or halogen, nitro, alkoxy or —NHCOCH$_2$NHCH$_3$; R and R$_0$ are independently H, halogen or a moiety of one of the following formulas:

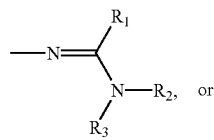

(Ia)

or

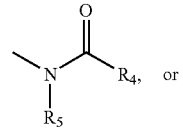

(Ib)

or

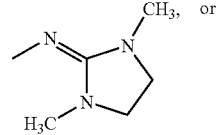

(Ic)

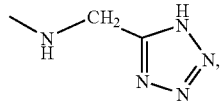

(Id)

or —N=CHOC$_2$H$_5$ or —(CH$_2$)$_q$CN where q is an integer from 1 to 5;

wherein R$_1$ is hydrogen, or linear or branched alkyl; cycloalkyl or aryl rings, which cycloalkyl or aryl rings can comprise one or more heteroatoms selected from O, N and S and which cycloalkyl or aryl rings can be substituted with linear or branched alkyl halo, nitro or amino; or R$_1$ is a moiety of the formula:

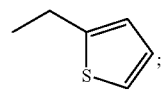

(Ie)

$R_2$ is hydrogen, alkyl or branched alkyl or benzyl;

$R_1$ and $R_2$ taken together may be —$(CH_2)_p$— where p is an integer from 2 to 4 and wherein $R_3$ is methyl;

$R_3$ is alkyl, branched alkyl, or cycloalkyl;

$R_4$ is linear or branched alkyl optionally substituted with 1 or more halogen, amino or alkylamino; or aryl optionally substituted with one or more alkyl, halo, nitro or amino moieties; —$(CH_2)_q$CN where q is an integer from 1 to 5, —$CH_2COR_6$ or —$CH_2$—$NR_7R_8$;

$R_2$ and $R_3$ taken together with the associated nitrogen can be pyrrolidino, piperidino, morpholino, thiomorpholino, 4-methylpiperazino, 3-azabicyclo[3.2.2]nonyl, azetidino or azaspiro[5,5]undecanoyl;

$R_5$ is hydrogen, alkyl or branched alkyl; and $R_6R_7$ and $R_8$ are independently hydrogen, or linear or branched alkyl optionally substituted with 1 or more halo, nitro or amino groups;

and pharmacologically acceptable salts thereof.

The compositions employed in the present invention include: (i) one or more compounds described by Formula (I) or Formula (II), preferably those compounds of Formula (II) described by Formula (III); (ii) one or more cells collected from an animal or organism subsequent to administration of a compound of (i) to the animal or organism; or (iii) any combination of (i) and (ii). Preferably the tissue is neural tissue, liver tissue, pancreatic tissue or muscle tissue.

The invention also provides methods for promoting tissue regeneration or neural expression comprising administering to a first mammal a tissue expression promoting effective amount or a neural regeneration effective amount of a composition of the invention, collecting cells from the first mammal and delivering them to a site of injury in the first mammal or in a second mammal. In some embodiments, repeated administration of a tissue expression promoting amount of a composition of the invention can total an accumulated administration of a tissue regeneration effective amount. In preferred embodiments, administration of a tissue expression promoting effective amount, more preferably a single administration, of a composition of the invention can constitute a tissue regeneration effective amount. Preferably the tissue is neural tissue.

Compounds of Formula (II) with the following formula (III) can be prepared in accordance with the reaction scheme taught in U.S. Pat. No. 4,532,349, which is incorporated herein by reference:

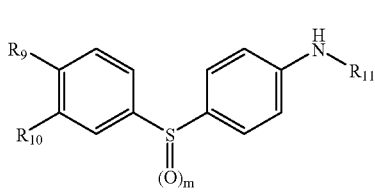
(III)

wherein m=0, or 2; $R_9$ is hydrogen, fluoro, chloro, bromo, nitro, alkoxy or —$NHCOCH_2NHCH_3$; $R_{10}$ is hydrogen or chloro; and $R_{11}$ is —$CH_2CN$, —$COCH_2NH_3$, —$COCH_2NHCH_3$, —$COCH_2Cl$, —$COCH_2CH_2Cl$ or —$C(O)R_{12}$ wherein $R_{12}$ is alkyl group having up to 4 carbon atoms such as methyl, isopropyl, n-butyl, and the like.

Compounds of Formula (I) with the following formulas (IV, V, VI) can be prepared in accordance with the reaction schemes taught in U.S. Pat. No. 4,965,284, and European Patent Application EP 0 342 433 A2:

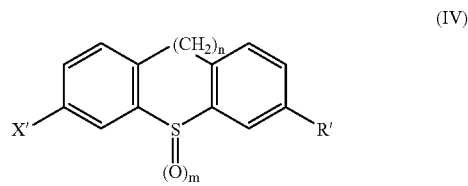
(IV)

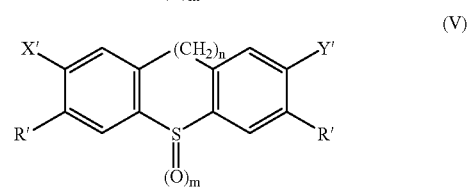
(V)

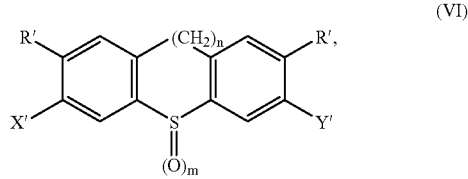
(VI)

wherein n, m, R', X' and Y' are defined as follows:

n is 0 or 1; m is 0, 1, or 2; X' is hydrogen, fluoro, chloro or bromo; Y' is hydrogen, fluoro, chloro or bromo; R' is a moiety of one of the formulas:

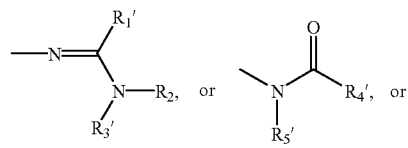

R' may also be —N═CHOC2H$_5$, or

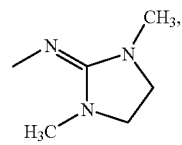

$R_{1'}$ is hydrogen, alkyl or branched alkyl ($C_1$-$C_6$), phenyl, substituted phenyl, pyridine, thiophene or

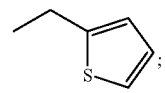

$R_{2'}$ is hydrogen, alkyl or branched alkyl ($C_1$-$C_6$) or benzyl;

$R_{3'}$ is alkyl or branched alkyl ($C_1$-$C_6$) or cycloalkyl ($C_3$-$C_6$);

$R_{4'}$ is alkyl ($C_1$-$C_6$) or branched alkyl, phenyl, substituted phenyl, —$CH_2C(O)CH_3$, or —$CH_2$—$N$—$(CH_3)_2$;

$R_{5'}$ is hydrogen, alkyl or branched alkyl ($C_1$-$C_6$);

$R_{1'}$ and $R_{2'}$ taken together is —$(CH_2)_q$— wherein q is an integer from 2 to 5; and $R_2$, and $R_3$, taken together with the associated nitrogen is pyrrolidino, piperidino, morpholino, thiomorpholino, 4-methylpiperazino, 3-azabicyclo[3.2.2]nonyl, azetidino or azaspiro[5,5]undecanoyl.

U.S. Pat. No. 4,965,284 and European Patent Application EP 0 342 433 A2 are incorporated herein by reference.

Some compounds of Formulas (I) and (II) above can be synthesized according to methods well known in the art. For example, some of the compounds used in the present invention can be prepared in two stages. The first stage involves the synthesis of tricyclic amine (or diamine) precursors (Schemes 1-6). The second stage produces the compounds used in the present invention by further elaboration of the amine moieties of the tricyclic precursors. (Scheme 7)

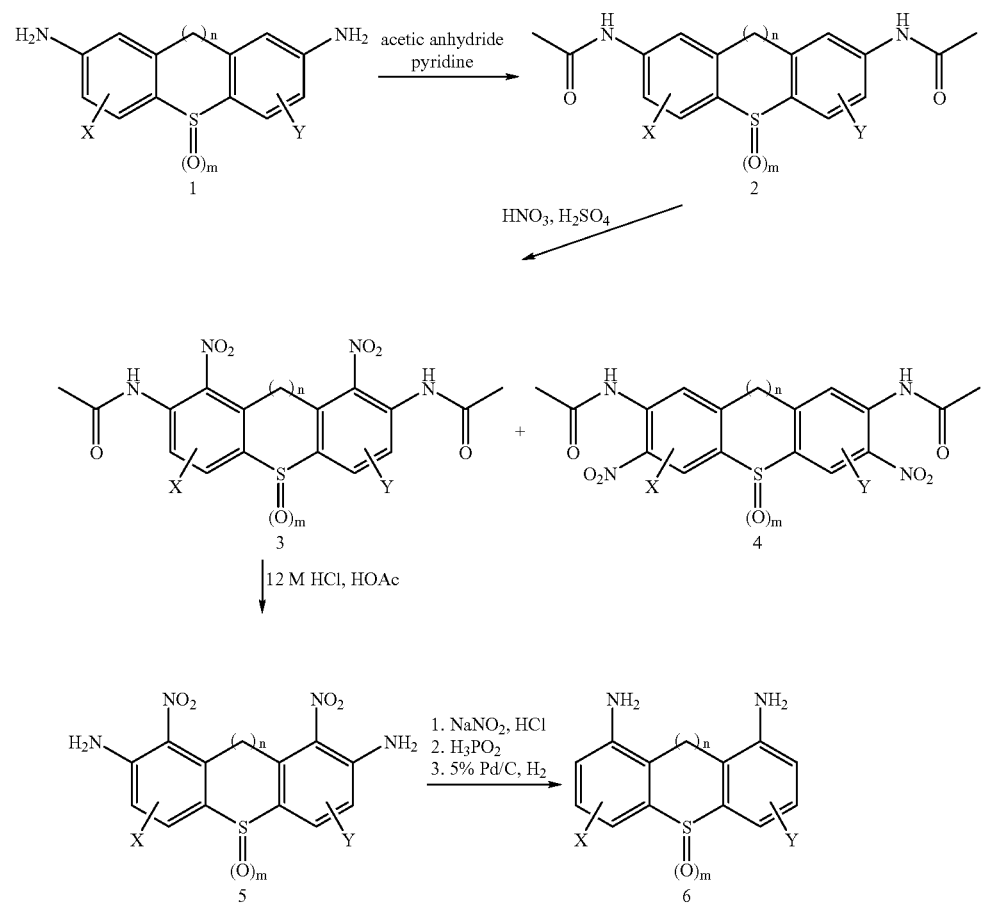

Scheme 1.
Preparation of 1,9-Diamino-dibenzothiophene(thioxanthene) (oxide) Analogs In the first stage the synthesis of tricyclic amine (or diamine) precursors is accomplished. Tricyclic intermediates of the general formula 6 can be prepared by Scheme 1. For example, 2,8-dibenzothiophenediamine S,S-dioxide can serve as an appropriate starting material for the steps drawn in Scheme 1. The preparation of the 2,8-dibenzothiophenediamine S,S-dioxide is described in EP 0 342 433. The 2,8-diamino groups of intermediate 1 can be acetylated yielding a bisacetamido intermediate 2. The intermediate 2 can be nitrated using nitric acid and sulfuric acid to yield mixtures of dinitro intermediates 3 and 4 from which the desired intermediate 3 can be isolated. Hydrolysis of the acetamido groups of 3 with hydrochloric acid releases the 2,8 diamino groups to give intermediate 5. The diamino groups of intermediate 5 are sequentially diazotized with sodium nitrite and HCl and reduced with hypophosphorous acid. The 1,9-dinitro group can then be catalytically hydrogenated with 5% palladium on carbon to afford the desired intermediate 6.

Scheme 2.
Preparation of 4,6-Diamino-dibenzothiophene/thioxanthene (oxide) Analogs

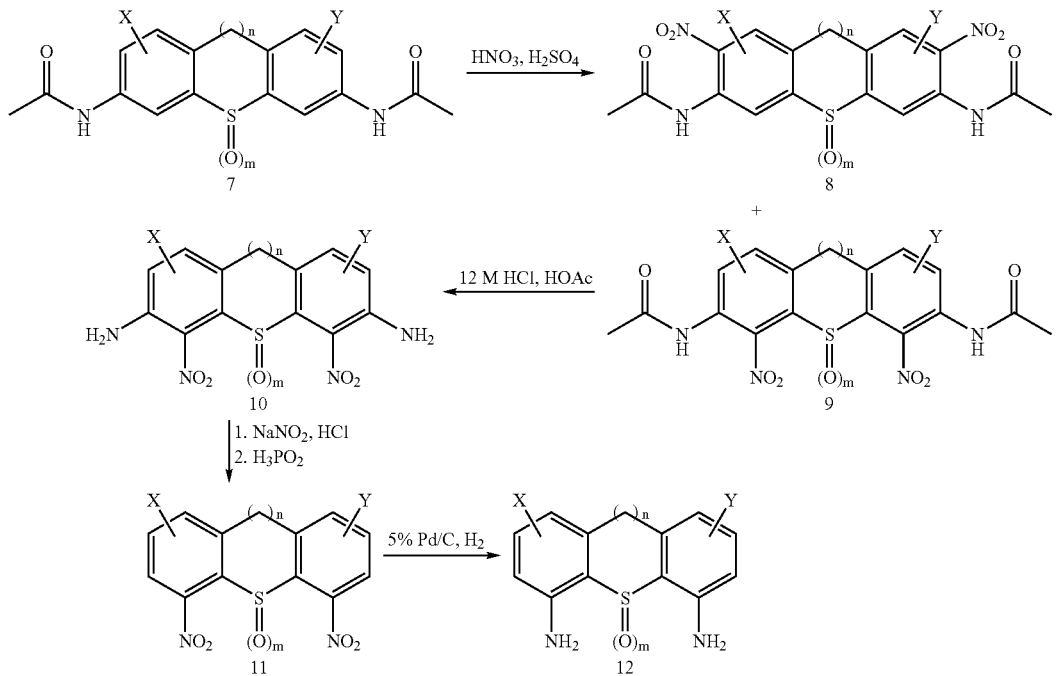

Tricyclic intermediates of the general formula 12 can be prepared according to Scheme 2. For example, N,N'-3,6-thioxanthenediylbisacetamide-10,10-dioxide can serve as an appropriate starting material for the steps drawn in Scheme 2. The preparation of N,N'-3,6-thioxanthenediylbisacetamide-10,10-dioxide is described in EP 0 342 433. The intermediate 7 can be nitrated using nitric acid and sulfuric acid to yield mixtures of dinitro intermediates 8 and 9 from which the desired intermediate 9 can be isolated. Hydrolysis of the acetamido groups of 9 with HCl releases the 3,7 diamino groups to give intermediate 10. The diamino groups of intermediate 10 are diazotized with sodium nitrite and HCl, and then reduced with hypophosphorous acid to furnish intermediate 11. The 4,6-dinitro groups of intermediate 11 are then catalytically hydrogenated with 5% palladium on carbon to afford the desired intermediate 12.

Scheme 3.
Preparation of 4-Amino Dibenzothiophene/thioxanthene (oxide) Analogs

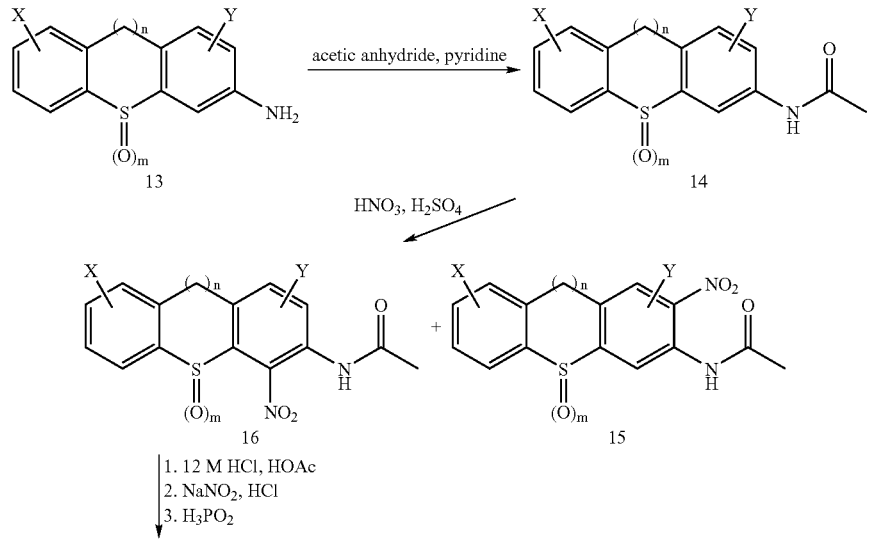

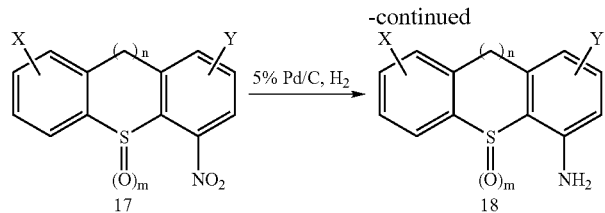

The preparation of 4-amino substituted intermediates 18 from 3-amino substituted intermediates 13 is described in Scheme 3. 3-Aminodibenzothiophene S,S-dioxide, for example, can be an appropriate starting material for this synthetic scheme. Preparation of 3-aminodibenzothiophene S,S-dioxide is described in EP 0 342 433. Acetylation of 13 with acetic anhydride in pyridine affords the acetamido intermediate 14. Compound 14 can be mono nitrated using nitric acid and sulfuric acid to provide a mixture of intermediates 15 and 16, from which 16 can be isolated. The acetamido group of intermediate 16 can be hydrolyzed using concentrated hydrochloric and acetic acid. The 3-amino group is then diazotized and the resulting diazonium salt is reduced using hypophosphorous acid to provide the 4-nitro intermediate 17. The 4-nitro group of intermediate 17 can be catalytically reduced to furnish the 4-amino intermediate 18. Preparation of 1-amino substituted intermediates such as intermediate 24 (Scheme 4) can be accomplished using a similar reaction scheme from 2-amino substituted intermediates 19.

The preparation of amino thioxanthene and its corresponding oxides can be accomplished from monocyclic precursors (Scheme 5). 6-Substituted methyl salicylates 25 are useful starting materials for the preparation of amino thioxanthenes. It can be recognized that numerous substituted salicylic acid derivatives are commercially available, or are readily prepared. Activation of the phenolic hydroxy group of 25 using p-toluenesulfonyl chloride in pyridine affords sulfonate 26. Coupling of sulfonate 26 with an alkali metal salt of a substituted thiophenol 27 provides the thioether 28. After saponification of the methyl ester of 28, dehydrative ring closure can be accomplished using, for example, a mixture of phosphorous pentoxide and methane sulfonic acid to furnish 29. The carbonyl group of 29 can be reduced with sodium borohydride and the nitro group(s) reduced catalytically using 5% palladium on carbon to provide the amino-substituted thioxanthene 30. Alternatively, an oxidation step of the sulfur moiety using meta Scheme 4.
Preparation of 1-Amino Dibenzothiophene/thioxanthene (oxide) Analogs

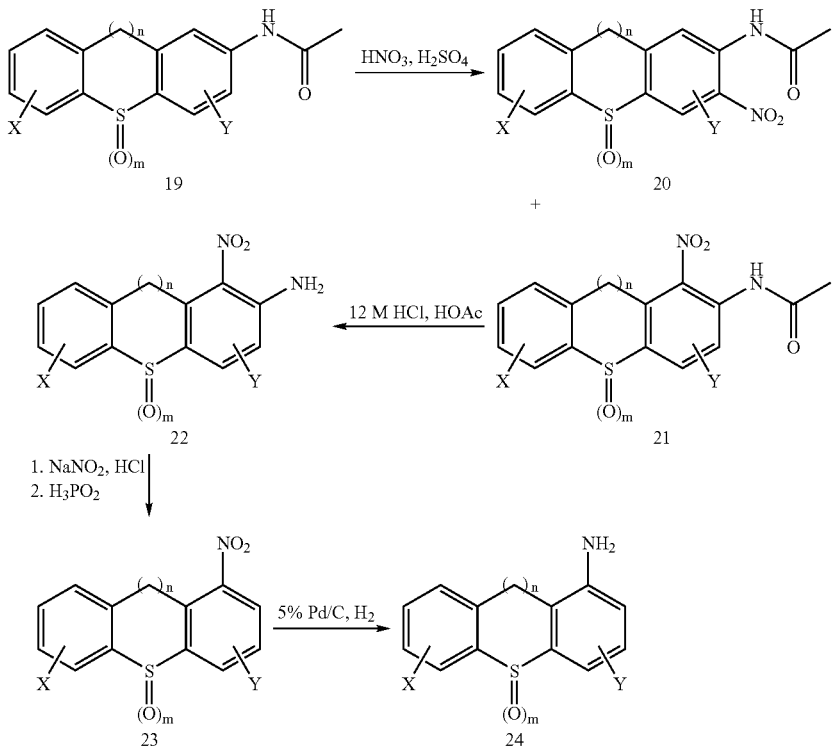

chloroperoxybenzoic acid on intermediate 29 can precede the reduction steps to provide the mono oxide and dioxide analogs 31.
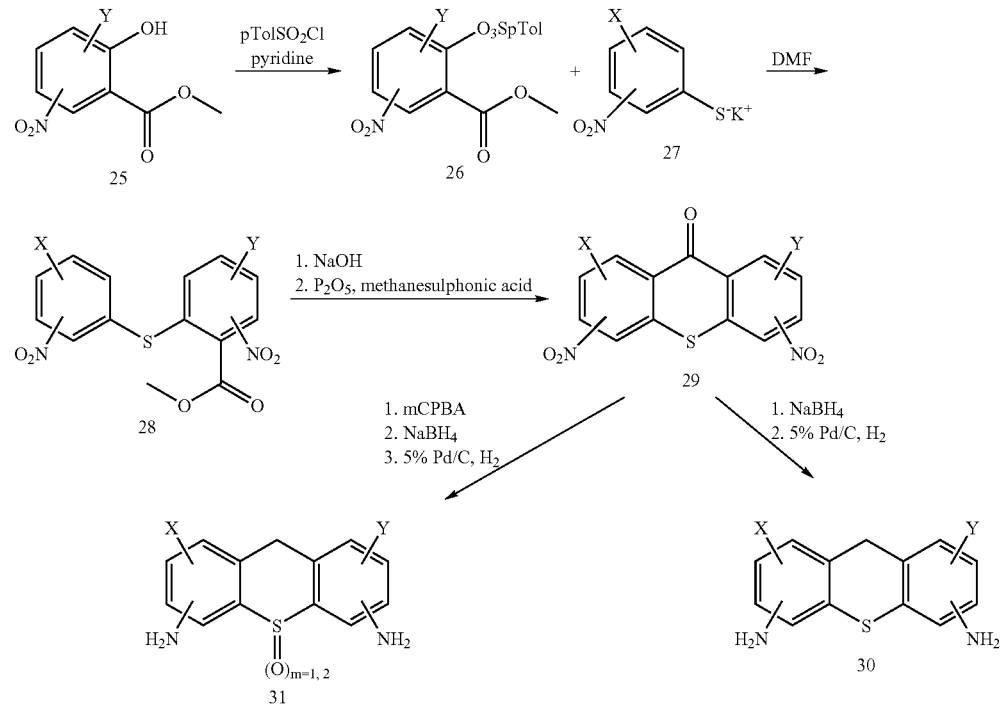
Scheme 5.
Alternate Preparation of Amino Thioxanthenes and Thioxanthene Oxides
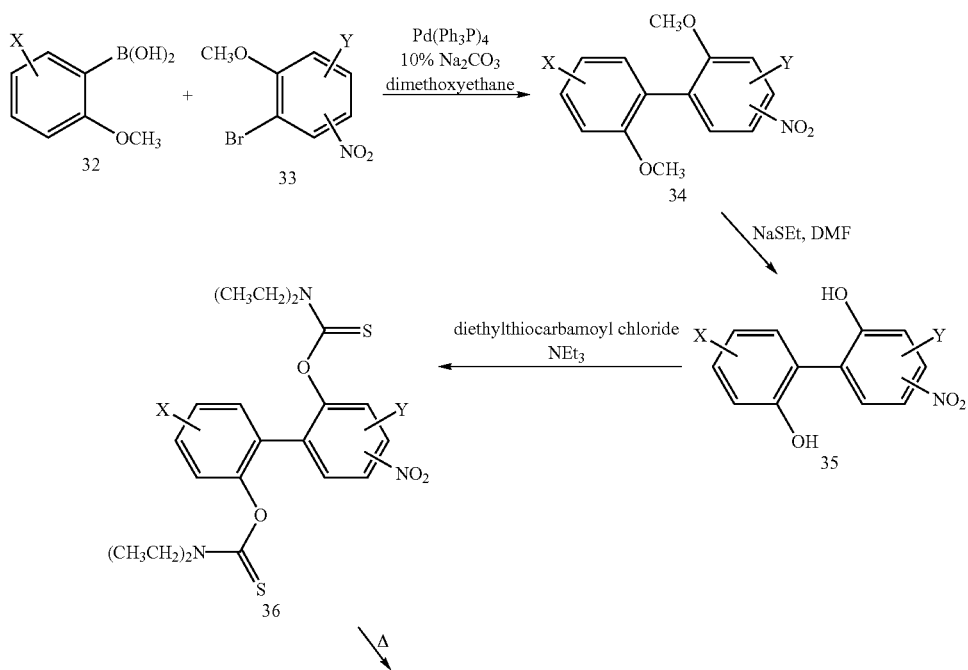
Scheme 6.
Alternate Preparation of Amino Dibenzothiophenes

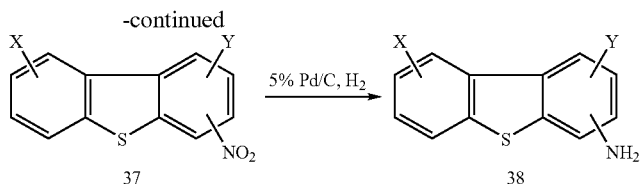

Alternative preparations of amino dibenzothiophenes (and their oxides) such as intermediate 38 from monocyclic precursors also exist. For example, in Scheme 6, the preparation of an amino substituted dibenzothiophene 38 is shown from an ortho methoxy substituted boronic acid 32 and a substituted bromoanisole 33. A Suzuki coupling using palladium tetrakis(triphenylphosphine) as a catalyst furnishes biaryl intermediate 34. (It can be recognized that alternative biaryl coupling protocols exist. For example, Stille-type couplings and Ullman couplings use different reaction conditions and different substrates.) The methoxy groups of intermediate 34 can be removed using sodium ethanethiolate in N,N-Dimethylformamide (DMF). Activation of the phenol groups of intermediate 35 with diethylthiocarbamoyl chloride can provide intermediate 36. Ring closure can be accomplished by heating intermediate 36 to provide the tricyclic intermediate 37. The nitro group of intermediate 37 can be reduced catalytically using 5% palladium on carbon to afford the desired aminodibenzylthiophene 38.

Scheme 7.
Preparation of Amidine Analogs from Aromatic Amines

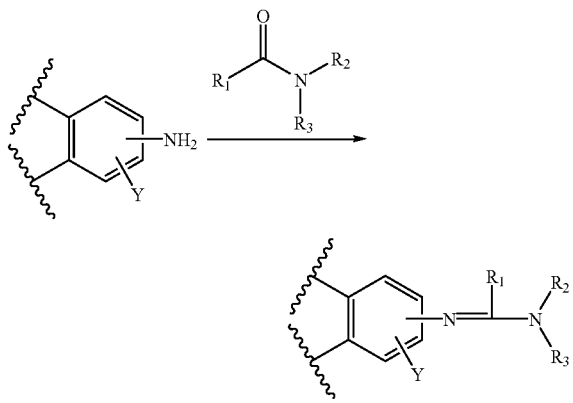

The second stage of the preparation is the substitution of aromatic amines (Scheme 7). These procedures are taught in U.S. Pat. No. 4,965,284, European patent applications EP 0 342 433, EP 0 354 303, and EP 0 394 542. Specifically, the preparation of the amidino type analogs from aromatic amines is described in EP 0 342 433 and EP 0 354 303 and is shown in Scheme IA. The preparations of alkane amido type analogs from aromatic amines are taught in U.S. Pat. No. 4,965,284, and in European patent applications EP 0 394 542 and EP 0 342 433.

Without being limited to theory, it is believed that the compositions and methods of the invention induce replacement of neurons, glial cells or both by stimulating endogenous populations of progenitor cells to differentiate into neurons, glial cells or both. The invention is not limited in scope to the nervous system. Progenitor cells may originate from neural or non-neural tissue (e.g., bone marrow cells). The invention can include compositions and methods for treating neurological conditions or diseases by replacement of neurons and/or glial cells by stimulating populations of neural progenitor cells to differentiate into neurons and/or glial cells. In some embodiments, it is believed that the compositions of the invention prime progenitor cells to differentiate into cells that are needed to ameliorate a pathologic condition such as a disease. Progenitor cells can include, but are not limited to, any pluripotent stem cell such as those found in bone marrow cells or the CNS. In some embodiments of the invention, administration of compositions of the invention that are preferably compounds of Formula (I) or Formula (II), more preferably compounds of Formula (II) that are described by Formula (III), to an animal results in amelioration or rectification of disease conditions or injury. For example, the oral administration of a compound of Formula (II) and Formula (III) can, in some embodiments, result in improvement or restoration of red blood cell counts in anemic animals to normal or near normal levels. In some embodiments of the invention, transplant of progenitor cells to an injury site from an animal that has been treated with a composition of the invention, preferably compounds of Formula (I) or Formula (II), can result in enhanced differentiation of these progenitor cells into the types of cells required at the site of injury compared to transplantation of similar cells from non-treated animals.

Exemplary compounds which can be used to practice the methods of the invention include, but are not limited to, the following:

N-[4-[(4-fluorophenyl)sulfonyl]phenyl]acetamide,
3,7-Dinitrodibenzothiophene S,S-dioxide,
3,7-Diaminodibenzothiophene S,S-dioxide,
N',N'''-3,7-Dibenzothiophenediylbis[N,N-dimethylpropanimidamide]S,S-dioxide,
3-Nitrodibenzothiophene S,S-dioxide,
3-Aminodibenzothiophene S,S-dioxide,
3-Aminodibenzothiophene S,S-dioxide diazonium fluoborate,
3-Fluorodibenzothiophene S,S-dioxide,
3-Fluoro-7-nitrodibenzothiophene S,S-dioxide,
7-Fluoro-3-dibenzothiopeneamine S,S-dioxide,
N-(7-Fluoro-3-dibenzothienyl)acetamide S,S-dioxide,
N'-(7-Fluoro-3-dibenzothienyl(N,N-dimethylpropanimidamide S,S-dioxide,
2-Dibenzothienylmethyl ketone,
2,8-Diacetyldibenzothiophene,
1,1'-(2,8-Dibenzothiophenediyl)bisethanone S,S-dioxide,
1,1'-(2,8-Dibenzothiophenediyl)bisethanone, dioxime S,S-dioxide,
N',N'''-2,8-Dibenzothiophenediylbisacetamide S,S-dioxide,
2,8-Dibenzothiophenediamine S,S-dioxide,
N,N'''-2,8-Dibenzothiophenediylbis[N,N-dimethylpropanimidamide] S,S-dioxide,
N,N'-(2,8-Dibenzothiophenediyl)bisacetamide, N,N'''-3,6-Thioxanthenediylbis[N,N-dimethylformamide] 10,10-dioxide dihydrochloride, N,N'''-Thioxanthene-3,6-diylbis-N,N-diethylformamide, N,N-Thioxanthene-3,6-diyldiformimidic diethyl ester, N',N'''-9H-Thioxanthene-3,6-diylbis-N,N-dimethylpropanimidamide 10,10-dioxide, N,N'''-9H-thioxanthene-3,6-diylbis-N,N-diethyl-propanimidamide S,S-dioxide, N',N'''-9H-Thioxanthene-3,6-diylbis-N,N-dimethylethanimidamide S,S-dioxide, N,N'-9H-thioxanthene-3,6-diylbisacetamide 10,10-dioxide, N,N'-Bis(1-methyl-2-pyrrolidinylidene)-2,8-dibenzothiophenediamine 5,5-dioxide, N,N'-Bis(1-methyl-2-pyrrolidinylidene)-3,7-dibenzothiophenediamine 5,5-dioxide, 4,4'-[2,8-Dibenzothiophenediylbis(nitriloethylidyne)]bismorpholine S,S-dioxide, N,N'-Dibenzothiophene-3,7-diyl)bis-]N-methylacetamide] S,S-dioxide, 3,7-Bis-acetacetamidodibenzothiophene 5,5-dioxide, 3,7-Bis(2-chloroacetamido)dibenzothiophene 5,5-dioxide, 3,7-Bis(2-dimethylaminoacetamido)-dibenzothiophene 5,5-dioxide, 2,2'-(3,7-Dibenzothiophenediyldiimino)bis-]N,N,N-triethyl-2-oxo-ethanaminium]dichloride S,S-dioxide, N'-2-Dibenzothienyl-N,N-diethyl-2-thiopheneethanimidamide, N,N-(2,8-Dichlorodibenzothiophen-3,7-diyl)bisbenzamide S,S-dioxide, N,N'-(5,5-Dioxodibenzothiophene-3,7-diyl)bisbenzenamide, N,N'''-2,6-Dibenzothiophenediylbis[N,N-dimethylpropanimidamide] S,S-dioxide, Particularly preferred compounds for practicing the methods of the invention include N-[4-[(4-fluorophenyl)sulfonyl]phenyl]acetamide and N,N'''-2,8-Dibenzothiophenediylbis[N,N-dimethylpropanimidamide] S,S-dioxide.

The neurons to be treated by the method of the invention are preferably CNS neurons, but non-CNS neurons can be susceptible to such treatment as well. Moreover, such treatment can be effective for ameliorating damage to the central or peripheral nervous system (PNS).

The method of the invention is exemplified by a first embodiment wherein administration of a single in vitro dose of N-[4-[(4-fluorophenyl)sulfonyl]phenyl]-acetamide, a compound according to Formula (II), to a population of mixed embryonic day 18 ("E18") rat neural cultures without living neurons results in a protein expression pattern within the culture that is indicative of development of neuronal cells from progenitor cells. The embryonic neural cultures are first subjected to glutamate excitotoxic exposure sufficient to result in neuronal cell death prior to administration of the compound. Cultures obtained from E18 rat embryos are allowed to mature in vitro for 10 days at which time they are treated with 10 mM glutamate to kill the neurons. Eight days later, cultures are treated with a range of doses of the compound N-[4-[(4-fluorophenyl)sulfonyl]phenyl]acetamide from 0.01 µg/ml to 100 µg/ml. In comparing control cultures and drug treated cultures, an antigenic marker for neuronal progenitor cells, e-NCAM (as detected by immunohistochemical methods), is elevated one week after treatment of the culture with N-[4-[(4-fluorophenyl)sulfonyl] phenyl]-acetamide. By three weeks post treatment, elevated levels of beta-tubulin expression are detected in large numbers of cells in cultures treated with the compound. In contrast, few cells demonstrate strong immunoreactivity for beta-tubulin in untreated control cultures. Low levels of MAP-II expression are also detected at 3 weeks post treatment in a large number of cells treated with the compound. In contrast, few cells in untreated cultures are observed expressing MAP-II immunoreactivity at 3 weeks post-treatment. By 4 weeks post treatment, a large number of cells treated with the compound can be observed expressing intense MAP-II and beta-tubulin immunoreactivity. In control cultures, few cells are observed expressing intense MAP-II and beta-tubulin immunoreactivity. Finally, by 6 weeks post treatment, intense immunoreactivity against phosphorylated form of the middle and high molecular weight forms of neurofilament protein (NF-PO$_4$) can be observed in numerous neurites in compound treated cultures, but only in a few NF-PO$_4$ positive cells in untreated cultures. E18 derived cultures at ten weeks post treatment show expression of the Low affinity Neuron Growth Factor Receptor. This expression pattern represents the normal sequence of events as neuronal cells develop from progenitor cells.

The method of the invention is also exemplified by a second embodiment in which N-[4-[(4-fluorophenyl)sulfonyl]phenyl]acetamide is administered in vitro to tissue from postnatal mammals. Treatment with N-[4-[(4-fluorophenyl) sulfonyl]phenyl]acetamide results in neuroregeneration as evidenced by immunostaining for beta-tubulin, eNCAM and MAP II. Neural tissue harvested from Post Natal day 5 (PND5) animals can be prepared in culture by the method above used with E18 cells, except that the cultures are not treated with glutamate because the neurons are unable to survive the culture preparation step. Using an assay system, cells can be treated with N-[4-[(4-fluorophenyl)sulfonyl] phenyl]acetamide 24 hours after the cultures are established. A similar sequence of events that was observed with the E18 cultures is observed with PND5 rat cultures. Enhanced expression of eNCAM is observed in PND5 cultures immunostained for eNCAM at one week post treatment in treated samples compared to untreated control samples. At four weeks post treatment, increased numbers of β-tubulin positive cells were detected in wells treated with N-[4-[(4-fluorophenyl)sulfonyl]phenyl]acetamide compared to untreated control wells. In PND5 cultures immunostained for MAP-II at six weeks post treatment, MAP-II expression is enhanced in treated samples compared to untreated control samples.

The method of the invention is also exemplified by a third embodiment in which astrocytes are passaged 3 times prior to in vitro treatment with the compound and samples derived from the whole cortex were compared to samples enriched for tissue from the subventricular zone. Cultures of highly enriched, passaged astrocytes treated in vitro with N-[4-[(4-fluorophenyl)sulfonyl]phenyl]-acetamide show beta-tubulin positive cells with neuronal morphologies. Likewise, beta-tubulin positive cells with neuronal morphology can also be observed in untreated control cultures, but at a significantly reduced level. In addition to the beta-tubulin positive cells with neuronal morphologies, many beta-tubulin positive cells that have an astrocyte-like morphology can be observed, along with beta-tubilin positive cells that demonstrate a hybrid neuronal-astrocyte morphology. These same types of beta-tubulin positive cells can be observed in untreated control cultures, but in significantly reduced numbers.

In one study, PND-5 day cultures generated from tissue isolated specifically from the subventricular zone were compared to cultures generated from the whole cortex. Twenty four hours after dissection, cultures were treated with the compound. Four weeks after treatment, cultures were immunostained with antibodies against β-tubulin or antibodies against MAP II. Greater numbers of β-tubulin positive cells and MAP II positive cells were detected in wells treated with the compound. Interestingly, more β-tubulin positive and MAP II positive cells were detected in cultures established from sub-ventricular tissue.

In preferred embodiments, the invention relates to regenerating nerve tissue in vivo. Methods of the invention include administering a therapeutically effective dose of a composition of the invention to a first mammal in need of neural regeneration. In some embodiments, a compound of Formula (I) or Formula (II) is administered, preferably orally administered, to a mammal in need of tissue regeneration, preferably neural tissue regeneration. In some embodiments, methods of the invention comprise administering a compound of Formula (I) or Formula (II) to a first mammal, harvesting cells from the first mammal after administration of the compound and subsequently delivering the harvested cells locally at a site where increased neural expression or increased neural regeneration is needed, wherein the injury site can be in the first mammal or in a second mammal. In some embodiments, the compositions of the invention can be administered intralesionally. Preferably, the harvested cells are from any type of stem cell, for example bone marrow cells. For example, bone marrow cells can be collected from a donor animal (e.g., a rat) within two weeks, preferably within three to seven days, after oral administration of N-[4-[(4-fluorophenyl)sulfonyl]phenyl]acetamide in a pharmaceutically acceptable carrier to the donor animal. These bone marrow cells can be implanted at the site of injury, for example, to the spinal cord of an injured recipient animal (e.g., inject 10-20 µl into the cyst at or near the site of spinal cord injury), which can be the same animal or a different animal from the bone marrow donor animal. The recipient animal can be treated with bromodeoxyuruuridine (BrdU), which is incorporated into certain cell nuclei that pass through interphase (S phase) of the cell cycle, on a week-on/week-off schedule. Harvesting the spinal cords of the recipient animals 12 weeks after bone marrow cell implantation and immunostaining of the spinal cord tissue shows incorporation of BrdU in cell nuclei, as well as expression of nestin, beta-tubulin and GFAP-proteins indicative of nerve cell regeneration.

In some embodiments of the invention, cells, preferably bone marrow cells, can be transferred from a first animal treated according to methods of the invention to a site of chronic spinal cord injury in the first animal or in a second animal. After systemic administration of N-[4-[(4-fluorophenyl)sulfonyl]phenyl]acetamide to a rat, bone marrow cells harvested from the rat 3-7 days later shows increased expression of Nestin compared to bone marrow from non-treated rats. In slides stained for Nestin, Nestin immunoreactive cells are observed at the edge of the injury cavity in the spinal cord in treated rats but not in untreated rats. In addition, saline-treated animals showed no immunoreactivity toward Nestin.

In another study, cavities are induced by compressive injuries to the spinal cords of rats. In the study, rats are either untreated, treated with a saline vehicle, or treated with N-[4-[(4-fluorophenyl)sulfonyl]phenyl]acetamide in a saline vehicle. In comparing the extent of closure of the cavities in the injured spinal cords, it was observed that the rat treated with the N-[4-[(4-fluorophenyl)sulfonyl]phenyl]acetamide in a saline vehicle showed the most extensive closure of the cavity in the spinal cord compared to the untreated or saline treated rats.

The methods of the invention do not preclude the combined therapeutic use of conventional (or non-conventional) drugs which act on the cholinergic system (the group of neurons which release the neurotransmitter acetylcholine), such as the anti-cholinesterase tetrahydroaminoacridine (THA).

Other pharmaceutical compositions falling within the scope of the present invention include combinations of the compounds described herein with other known neurotrophic or neuroprotective materials, utilizing the art-recognized effective concentrations or dosages of those materials. Such materials include gangliosides, nerve growth factor (NGF), fibroblast growth factor (FGF), somatomedins, benzodiazepines, kappa-receptor agonists, calcium channel blockers, and the like; excitatory amino acid receptor antagonists, such as MK-801 (Merck, Sharp and Dome), an antagonist of NMDA; non-excitatory amino acid analogues such as Diazepam; or antagonists against receptors such as kainate receptors, quisqualate receptors or N-methyl-D-aspartate receptors; or the use of hexacosanol in combination with antagonists of excitatory amino acid agonists, to reduce excitotoxic damage to neurons. (Foster, et al., Br. J. Pharm. Proc. Supp., 90:9P (1987); Wielock, Science, 230:681 (1985);Ben-Ari, et al., Brain Res, 165: pp. 362-365 (1979)).

The most effective mode of administration and dosage regimen for the compositions used in the methods of this invention will depend upon the severity and course of the injury or disease, the patient's health and response to treatment, and the judgment of the treating health professional. The optimal concentration is a function of a variety of factors, such as the desired frequency of application, mode of application, duration of effect, amount of repair and/or protection of neuronal tissue, severity of trauma or disease, results of toxicology studies, or the level of adverse side effects and considerations implicated by the chemical nature of the compound or its carrier. Accordingly, the dosages of the compositions can be titrated to the individual subject. Nevertheless, an effective dose can be in the range from about 10 mg/kg to about 500 mg/kg body weight; preferably from about 25 mg/kg to about 200 mg/kg; and, most preferably, from about 50 mg/kg to about 100 mg/kg. The exact dosage of the compositions of the methods of the invention for any particular application can be determined by standard animal and clinical testing techniques. The dosage unit compositions will contain a pharmaceutically-effective amount of the active ingredient.

The compositions and methods of the invention can be administered or performed prior to, concurrently with, or following the incidence of trauma or onset of disease. Thus, the compositions of the invention or analogues thereof can be introduced in vivo preceding injury; for example, before surgery, for the purpose of obtaining a protective effect against neuron disease, injury or death. The administration of treatment can also be performed at regular pre-set intervals preceding the injury. Appropriate timing of the administration of the compositions of the invention can be determined clinically in patients by a skilled professional or in animal models. For preventative treatment, a patient suspected of propensity for the disease can be tested, for example, by genetic testing methodology; and appropriate dosages can then be administered.

Compositions of the present invention can be administered in vivo using conventional modes of administration which include, but are not limited to, intraperitoneal, intrathecal, intravenous, intracerebral, intramuscular, intralesional or intraventricular injection; or they can be administered topically, orally, sublingually, bucally, vaginally, parenterally, or via implantation or infusion methods.

Parenteral compositions can be provided containing the active composition and any of the well-known injectable carriers. The term "parenteral" as used herein includes subcutaneous injection, intravenous, intramuscular, intrathecal, intralesional or intrasternal injection; or infusion techniques. For parenteral administration, carriers such as saline, glucose, phosphate buffered saline, and the like may be used. For parenteral administration in an aqueous solution, for example, the solution should be suitably buffered if necessary and the liquid diluent first rendered isotonic with sufficient saline or glucose. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences"15th Edition, pages 1035-1038 and 1570-1580). Some variation in dosage will necessarily occur depending on the condition of the subject being treated. The person responsible for administration will, in any event, determine the appropriate dose for the individual subject.

For intrathecal or intralesional administration, carriers for parenteral administration, particularly carriers such as glucose in water or saline are appropriate. The compositions may also be prepared in liposomes to enhance transfer across membrane barriers. The compositions of the invention can be used in combination with any pharmaceutically acceptable carrier that promotes, enables or allows transfer of the composition across the blood brain barrier. Of course, compositions for parenteral use, including compositions for intravenous, intramuscular, subcutaneous or intrathecal administration, will be provided in sterile solutions.

The parenteral composition includes not only the active ingredient but can also include a physiologically-acceptable surface active agent, either ionic or non-ionic, as well as conventional preservatives. Injectable carriers can be solvent or dispersion media containing, for example, water, ethanol, glycerol, hydroxymethylcellulose, propylene glycol, polyethylene glycol, polyoxyethylenesorbitan, and vegetable oils. The carrier can also include pharmaceutically-acceptable carriers known in the art, such as alcohols, albumin proteins, or other appropriate carriers which can include pharmaceutically-advantageous adjuvants, such as preservatives, antibiotic or antimitotic agents, buffers, osmotic balancers, water, or electrolytes. A pharmaceutically- or physiologically-acceptable injectable carrier within the scope of the present invention will meet industry standards for sterility, isotonicity, stability, and non-pyrogenicity. The injectable solutions can include conventional antibacterial or antifungal agents, such as parabens, chlorobutanol, phenol, sorbic acid, thimerosal, and the like. Buffers can be used to maintain the composition at physiological pH or at a slightly lower pH (e.g., 5 or 6). The solutions can be made isotonic by the addition of conventional materials, such as sodium chloride and/or sugars. Surface active agents can be selected from the conventional categories of those materials, including polyoxyethylenes or polyoxyalkylenes, sorbitan derivatives, and the like. Other solubilizing agents include proteinaceous solubilizers, such as albumin, and water-miscible alcohols, such as ethanol.

Compositions may be prepared for transdermal administration via patches. Solvents which are also used for administration of hydrophobic compounds may also be used for this purpose such as DMSO or oils which cross the dermal barrier.

In some embodiments, the compositions of the invention can be formulated as a pharmaceutical composition that can be in any form suitable for oral use, such as tablets, suspensions, dispersable powders, emulsions, capsules, or elixirs. Coloring, flavoring, sweetening, and preserving agents also can be provided. In a preferred embodiment, compositions comprising compounds of Formulas (I) or (II) of the invention are formulated into oral compositions, and can be provided in individual dosage units. However, any composition of the invention of the present invention may be provided in individual dosage unit. Each unit can contain a pharmacologically-effective amount of active ingredient.

Tablets containing the active ingredient or ingredients—preferably compositions comprising compounds of Formulas (I) or (II) of the invention—in a mixture with non-toxic pharmaceutically-acceptable excipients which are suitable for the manufacture of tablets are also within the scope of this invention. These excipients can be inert diluents, such as calcium carbonate, sodium carbonate, lactose, calcium phosphate; or binding agents, such as starch, gelatin, or acacia; or lubricating agents, such as magnesium stearate, stearic acid, or talc. Moreover, oral compositions can be coated by known techniques to delay disintegration and absorption in the gastrointestinal tract, thereby providing sustained action.

Aqueous suspensions of compositions of the instant invention are provided by the invention, which aqueous suspensions can contain conventional suspending agents, dispersing agents, or wetting agents; preservatives, coloring agents, flavoring agents, and sweetening agents formulated in accordance with industry standards. Similarly, dispersable powders and granules for preparation of aqueous suspensions by the addition of water can be provided.

In some embodiments, the compositions of the methods of the invention can be introduced into the region of injured neurons by means of implanted polymers impregnated with the compositions; for example, Elvax.RTM. (Dupont, Wilmington, Del.) for release of the compositions over time. The compositions can include conventional pharmaceutically-acceptable carriers known in the art, such as alcohols (e.g., ethyl alcohols), serum proteins, human serum albumin, liposomes, and buffers (including phosphates), water, sterile saline or other salts, or electrolytes.

Administration of the compositions to humans, in the methods of the invention, can, of course, be performed after standard toxicity studies to determine any toxic effects and safe dosages for treatment.

Greater amounts of the active compound can be used in controlled release compositions that release their active ingredient over a period of more than about 12 hours. Any of the conventional controlled-release vehicles can be used to advantage, including bioerodable materials, such as collagen, polylactic acid, and the like. Other controllable release materials include lattice-forming polymers, such as polymethylmethacrylate, gelatin, cellulosic materials, and the like.

Conditions resulting in the need for neuronal replacement in a subject can be the result of, for example, any type of trauma to the neurons, which can include trauma as a result of surgery or accident, or as a result of neurodegenerative disease, chemotherapy or irradiation therapy.

The compositions and methods of the invention can be useful in treating any number of conditions that result from nerve cell pathology or death, including but not limited to: CNS injury including compressive spinal cord injuries, neurodegenerative diseases and conditions, loss of learning or memory function and excitotoxic nerve injury. Accordingly the following may be mentioned as nonlimiting examples of neurodegenerative diseases and conditions which the methods and compositions of the invention can be useful in treating: various diseases accompanying cerebrovascular disorders including cerebral hemorrhages such as hypertensive intracerebral hemorrhage and subarachnoid hemorrhage, transient cerebral ischemic attacks, cerebroarteriosclerosis and their sequela, or neurodegenerative diseases such as Alzheimer's Disease, Parkinson's Disease, amyotrophic lateral sclerosis, Down's syndrome, Huntington chorea and spinal cerebellar degeneration, as well as brain damages at the time of revivification after cardiac arrest, brain dysfunction prior to or after brain surgery, disorders of the nervous system due to hypoxia, hypoglycemia, brain or spinal damage, intoxication with drugs or gases, diabetes mellitus, administration of anti-cancer agents, alcohol and the like, senile dementia and dysplasia.

The methods of the invention can be useful in providing a promising approach for treatment of spinal cord injuries. As a non-limiting illustration of an embodiment of the invention, compounds of the methods of the invention that promote the differentiation of progenitor cells can be orally administered to a first mammal that has sustained a spinal cord injury. Subsequent to administration of the compound, bone marrow cells from the first mammal can be harvested and injected at the site of spinal cord injury.

In some embodiments, the methods of the invention can be useful in improving conditions at the site of CNS injury so as to minimize acute neuronal damage and thereby reduce functional loss and promote neuroregeneration. Methods of the invention can be combined with treatments currently in use that are designed to reduce the damaging effects of tissue ischemia, such as adminstration of steroid hormones, naloxone, and thyrotropin-releasing hormones. If the severity of the necrotizing histopathological reaction can be reduced in this way, it is possible to design treatment protocols in which spinal injuries are treated initially with drugs designed to reduce edema and ischemia and, subsequently, with agents designed to promote axonal growth.

Treatment of a CNS injury, such as a spinal cord injury, can focus on either limiting the damage produced acutely by the initial injury, or promoting the regeneration of axons during the later stages after injury (De Latorre, Spine, 6:315 (1981)): The histopathological changes at the site of injury can, in some instances, be described as progressive ischemic necrosis; they are initiated by an inadequate vascular perfusion of the injured tissue that results in cell death, cystic degeneration, and cavitation. This necrotizing process can continue for weeks and even months; as a result, the initial narrow, well-circumscribed lesion can become as long as several vertebral segments. During this time, fibroblasts and astrocytes will proliferate and invade the spinal cord and surrounding tissue, forming a fibrous meshwork that segregates the necrotic region from the normal tissue; this environment can certainly impair the possibility of axonal growth into the lesion. The compositions and methods of the invention reduce the size of cavities induced as a result of spinal cord injury, and promote the expression of proteins therein that are indicative of neural tissue cell growth or neural tissue cell differentiation from progenitor cells, suggesting utility in ameliorating spinal cord injuries.

The methods of the invention can be useful in treating acute forms of neurodegeneration caused, for example, by stroke and brain trauma, and chronic forms of neurodegeneration such as Alzheimer's disease, Parkinson's disease, Huntington's disease, ALS (amyotrophic lateral sclerosis) and neurodegeneration associated with bacterial or viral infections. Parkinson's Disease results mainly from degeneration of dopamine releasing neurons in the substantia nigra of the brain and the resulting depletion of dopamine neurotransmitter in the striatum. The cause of this degeneration is unknown but the motor degeneration symptoms of the disease can be alleviated by peripherally administering the dopamine precursor, L-dopa, at the early onset of the disease. As the disease continues to worsen, L-dopa is no longer effective and currently no further treatment is available. Alzheimer's Disease (AD) is a pathology characterized by an early and extensive loss of entorhinal cortex neurons. AD patients may be identified by progressive and degenerative effects on the brain which cannot be attributed to causes other than AD. AD is characterized by the presence of numerous amyloid plaques and neurofibrillary tangles (highly insoluble protein aggregates) present in the brains of Alzheimer's disease patients, particularly in those regions involved with memory and cognition. The methods of the invention can also be useful in treatment of nerve cell degeneration resulting from chemotherapy and radiation therapy affecting the nervous system as well as various demyelinating neurodegenerative conditions and diseases, including without limitation neuronal dysfunctions associated with aging, diabetic neuropathy, Alzheimer's disease, hereditary hemorrhage with amyloidosis-Dutch type, cerebral amyloid angiopathy, cerebral amyloid angiopathy, Down syndrome, spongiform encephalopathy, Creutzfeld-Jakob disease, HIV infection related neuropathies, AIDS dementia, Parkinson's disease, multiple sclerosis, amyotrophic lateral sclerosis (ALS or Lou Gehrig's disease), stroke, or trauma.

Methods of treating neurodegenerative conditions that induce neuronal replacement not only restore neuronal function, but also hold benefits of ameliorating or reversing the course of impaired facilitation of learning and memory associated with such neurodegenerative conditions. Successful outcomes from treatment of injured neurons includes recovery of behavioral functions of the neurons. Damage to specific brain areas from trauma or disease can preferentially compromise learning or memory functions, including higher cognitive functions.

The invention can be useful in providing methods for treating conditions associated with excitotoxic nerve injury. Permanent injury to the central nervous system (CNS) occurs in a variety of medical conditions. Excitotoxic injury is believed to be a fundamental cause of neural loss in anoxic and ischemic brain damage, hypoglycemic brain damage, seizure-mediated brain damage, and possibly damage in Huntington's Disease and Neurolathyrism, as well as a complication in Alzheimer's Disease (see Rothman and Olney, Trends in Neuroscience, 7:299-302 (1987)). It is known that the brain has high metabolic requirements, and that it can suffer permanent neurologic damage if deprived of sufficient oxygen (hypoxia) for even a few minutes. In the absence of oxygen (anoxia), mitochondrial production of ATP cannot meet the metabolic requirements of the brain and tissue damage occurs. This process is exacerbated by neuronal release of neurotransmitter glutamate, which stimulates NMDA (N-methyl-D-aspartate), Ampa (alpha-amino-3-hydroxy-5-methyl-4-isoxazole propionate) and kainate receptors. Activation of these receptors initiates calcium influx into the neurons, and production of reactive oxygen species, which are potent toxin that damages important cellular structures such as membranes, DNA and enzymes. The brain has many redundant blood supplies, which means that its tissue is seldom completely deprived of oxygen, even during acute ischemic events caused by thromboembolic events or trauma. A combination of the injury of hypoxia with the added insult of glutamate toxicity is therefore believed to be ultimately responsible for cellular death. Anti-oxidants and antiinflammatory agents have been proposed to reduce damage, but they often have poor access to structures such as the brain, which is protected by the blood brain barrier.

The compositions and methods of the invention can be useful in treatment of excitotoxic injury to nervous system tissue. Lucas and Newhouse (A.M.A. Arch. Ophthalmol., 58:193 (1957)) demonstrated that peripheral administration of the amino acid glutamate causes degeneration in the inner layers of the retina. Subsequently, Olney, et al. (Exp. Brain Res., 14:61-76 (1971)) showed that administration of glutamate produced damage to the brain, particularly the hypothalamic region. It was suggested that, in view of the high concentrations of L-glutamate found in the brain, the accumulation of excess glutamate might be a potential mechanism for neural loss in certain central nervous system (CNS) diseases. It was also found that the excitatory potency of a series of glutamate analogues correlated with their ability to cause neurotoxic damage leading to an excitotoxicity hypothesis of CNS damage (Id.).

It has been shown that neuronal pathology induced by various excitotoxins is quite similar to a wide spectrum of neurological insults. Glutamate analogue kainate (KA) injections, for example, cause striatal degeneration of gamma-amino butyric acid neurons while sparing dopamine, glutamate, and serotonin afferents to the region. This pattern is similar to the neurochemical profile observed in Huntington's Disease (Mason and Fibiger, Brain Research, 155:313-329 (1978); and Coyle, et al., In "Kainic Acid as a Tool in Neurobiology," McGeer, et al., (Ed.), Raven Press, N.Y. (1978)). KA injected intra-ventricularly also creates a profile of neuronal loss in the hippocampus similar to that found in epilepsy (e.g., hippocampal fields CA3, CA4, and CA1 are extremely susceptible while the dentate gyrus and area CA2 are largely spared (Nadley, et al., Nature, 271:676-677 (1978)). Axon-sparing lesions produced by excitatory amino acid activators are quite similar to neuronal damage found not only in Epilepsy and Huntington's Disease but also in anoxia, ischemia, and hypoglycemia (Greenamyre, supra; and Rothman and Olney, supra). Similar observations have been made for Alzheimer's Disease and even neuronal atrophy seen in schizophrenia (see Greenamyre, suora; and Olney, In "Excitatory Amino Acids in Health and Disease," Lodges (Ed.), Wiley & Sons, Ltd., England, pp. 337-352 (1988)).

The compositions and methods of the invention can be useful in promoting regeneration in various types of tissue including, but not limited to the liver, pancreatic and muscle tissue. In some embodiments, tissue regeneration is believed to occur by action of the compositions and methods of the invention on stem cells, preferably pluripotent stem cells, to promote the differentiation of these cells into the types of cells required to ameliorate, for example, physiological deficiencies, pathologic conditions or injuries.

The compositions and methods of the invention can be useful in promoting liver regeneration. Hepatocytes have a capacity to proliferate in vivo, directly or via faculative stem cell growth. Liver regeneration is achieved primarily by cell division of mature adult hepatocytes (See Grisham, J. W., et al., Cancer Res. 22:842 (1962)), which have a high capacity for clonal growth, as shown by hepatocyte transplantation experiments in ectopic sites (See Jirtle, R. L., et al., Cancer Res. 42:3000 (1982)), and in transgenic mouse models (See Rhim, J. A., et al., Science 263:1149 (1994)). It has been shown in several studies, however, that when liver is stimulated to regenerate while proliferation of mature hepatocytes is suppressed, faculative stem cells emerge and proliferate. (See, for example, Thorgeirsson, S. S., et al., Proc. Soc. Exp. Biol. Med. 204:253 (1993)). Such cells, sometimes referred to as "oval cells," can mature into hepatocytes in defined animal models or ductular structures composed of cells ("ductular hepatocytes") with mixed hepatocyte and bile duct epithelial markers. (See Gerber, M. A., et al., Amer. J. Path. 110:70 (1983) and Vandersteenhoven, A. M., et al., Arch. Pathol. Lab. Med. 114:403 (1991)).

Hepatic cells can be obtained from a patient by a variety of procedures, for example, during surgery or by means of a percutaneous needle biopsy of the liver. Needle biopsies are well established procedures. See, for example, Petersdorf, et al., Harrison's, Principles of Internal Medicine, $10^{th}$ Edition, 1983.

Media designed for the isolation and growth of hepatocytes are well known. A line of tissue culture products are available from GIBCO for carrying out the isolation and growth of hepatocytes. Appropriate procedures and media for the isolation and growth of other cell types are known to those in the art.

In order that the invention described herein can be more fully understood, the following examples are set forth. These examples are for illustrative purposes only and are not to be construed as limiting the scope of this invention in any manner.

EXAMPLE 1

In Vitro Experiment: Embryonic Day 18 Cortical Neuron Culture

CNS tissue was harvested from embryonic day 18 (E-18) rat pups (Taconic Labs) using sterile technique and was stored in ice cold Hank's Balanced Salt Solution (HBSS-Gibco). Brains were removed from the cranium of 10 embryos, and the meninges removed to expose the underlying cortex. Cortex was isolated from the rest of the brain and stored in ice cold HBSS. After all material was collected, the tissue was minced and trypsinized using 0.1% trypsin (Sigma) for 30 minutes at 37° C. Trypsin action was inhibited by adding 0.5 mg/ml soybean trypsin inhibitor (Gibco). Tissue was rinsed with HBSS and triturated using a flame narrowed Pasteur pipette coated with fetal bovine serum (FBS—Media Tech).

Dissociated cells were counted and plated into 24 well cluster plates in DMEM (MediaTech) plus 10% FBS (Media Tech) at a density of $5 \times 10^5$ cells per well. Twenty-four well cluster plates were coated with poly-D-lysine prior to adding cells. Cultures were maintained for 10 days in vitro using a 3-4 day feeding schedule where half the media was removed and replaced with fresh media.

On in vitro day (IVD) 10, glutamate (Gibco) (110 µl of 20 mM added to wells that contained 1 ml of media) was add to all wells except control wells to a final concentration 2 mM. Control wells were fed an equal amount of media minus the L-glutamate. Cultures were maintained for an additional 9 days using a 3-4 feeding schedule. On IVD-18, media was removed and replaced with Neurobasal (Gibco)+ B27 supplements (Gibco) and L-glutamine (Media Tech). The next day, IVD-19, N-[4-[(4-fluorophenyl)sulfonyl]phenyl]acetamide dissolved in 2-hydroxypropyl-β-cyclodextrin (Sigma) was added to cultures such that the final concentrations of the compound were either 100 µg/ml, 10 µg/ml, 1 µg/ml and 0.1 µg/ml or 10 µg/ml, 1 µg/ml 0.1 µg/ml and 0.01 µg/ml. Two sets of control wells were included in each experiment. One set of glutamate treated wells received an equal dose of 2-hydroxypropyl-β-cyclodextrin but without N-[4-[(4-fluorophenyl)sulfonyl]phenyl]acetamide. In initial studies, the second set of controls, those wells that did not receive glutamate were treated with 100 µg/ml N-[4-[(4-fluorophenyl)sulfonyl]phenyl]acetamide dissolved in 2-hydroxypropyl-β-cyclodextrin. After it became apparent that the optimal dose was approximately 0.1 µg/ml to 1 µg/ml N-[4-[(4-fluorophenyl)sulfonyl]phenyl]acetamide, the concentration of drug added to the control wells was reduced to 1 µg/ml.

Cultures were maintained for up to an additional 10 weeks. One to two 24 well cluster plates were immunostained every week using known antibody markers including anti-eNCAM (Developmental Studies Hybridoma Bank—hybridoma cell line was purchased and antibody containing supernatant was produced in house, (1:2)), anti-β tubulin (Sigma (1:800)), anti-MAP II (Stemberger Monoclonals Inc.—SMI (1:8000)), anti-neurofilament (phosphoralyated, medium and heavy chain—SMI. (1:8000)) and anti-low affinity NGF receptor (American Tissue Culture Collection—hybridoma cell line was purchased and antibody containing supernatant was produced in house, (1:2)). These antibodies were selected because they are accepted markers for detecting neurons in different stages of development and differentiation (See, e.g., A Caceres, L I Binder, M R Payne, P Bender, L Rebhun, and O Steward, "Differential subcellular localization of tubulin and the microtubule-associated protein MAP2 in brain tissue as revealed by immunocytochemistry with monoclonal hybridoma antibodies,"*J. Neurosci.* 1984 4: 394-410).

All plates were immunostained using the following protocol. Prior to removing 24 well cluster plates from the 37° C. incubator, 8% paraformaldehyde (Sigma) and MEM (Gibco) wash media was warmed to room temperature. One hundred microliters of 8% paraformaldehyde was added to each well and left to incubate for 10 minutes. Additional, 100 µl aliquots of 8% paraformaldehyde were added every 10 minutes until the final concentration of paraformaldehyde was 4%. After reaching 4%, the cultures were incubated with the paraformaldehyde for an additional 10 minutes after which the media was remove and all wells were washed 3 times×10 minutes with 1 ml of MEM. Following the final wash step, −20° C. ethanol (Fisher) was added to each well, the plate was placed in the −20° C. freezer for 10 minutes, after which the ethanol was removed and the cell layer was rehydrated with MEM. Primary antibodies were diluted with PBS and layered onto the cells. Plates were incubated with the primary antibody for 1 hour at room temperature after which the antibodies were removed and all wells were washed 3× with PBS. To visualized bound primary antibodies, rhodamine labeled antibodies (Jackson Immunolabs), were diluted with PBS, layered onto the cells and incubated for 30 minutes at room temperature. After the 30 minute incubation, all wells were washed 3× with PBS, hydrated with Fluorescent Mounting Medium (Dako) and covered with glass coverslips (Fisher).

EXAMPLE 2

In Vitro Experiment: Neonatal Astrocytes

Post natal day 5 rat pups (Taconic Labs) were decapitated, skin covering the cranium was removed so the bone over top the brain could be opened. Using a sterile spatula, the brain was extracted from the opened cranium and transferred to a 60 mm petri dish (Corning) containing sterile, ice cold Hank's balanced salt solution (HBSS). The meningial tissue was removed from the cortex, the cortex was gently teased away from the subcortical structures and transferred to a new 60 mm petri dish containing ice cold HBSS. Using a pair of fine, curved forceps, the desired cortical material was pinched from the remainder of the cortex and transferred to a new 60 mm petri dish containing ice cold HBSS. For most experiments, only tissue in the immediate vicinity of the subventricular zone was collected while in a few experiments, almost the entire cortex was pinched leaving only the outer most layer of cortical tissue behind. After harvesting all cortical tissue, the tissue was minced using two #11 scalpel blades that were repeatedly drawn across each other. After the majority of the tissue was minced into approximately 1 mm cubes, the HBSS was removed and replaced with 4 ml of trypsin/EDTA (Gibco—0.5%/5.3 mM) plus 1 ml of DNase (Sigma—0.01%). The petri dish containing tissue and enzymes were placed in a 37° C. incubator for 30 minutes and agitated every 5 minutes. After 30 minutes, the tissue was removed from the incubator and 1 ml 0.1 mg/ml of soybean trypsin inhibitor was added. Tissue was transferred to a 15 ml conical tube, spun at 500×g for 10 minutes in a refrigerated centrifuge. Supernatant was removed, the pellet was resuspended in 10 ml of DMEM+10% FBS, passed first through a 100 µm filter (Falcon) and finally through a 40 µm filter (Falcon). A cell count was performed to determine the final volume of media needed to yield a cell density of $1 \times 10^6$ viable cells per ml. Five hundred microliters of supernatant containing $5 \times 10^5$ viable cells was added to each well of 24 well cluster plates previously coated with 5 µg/ml poly lysine.

To remove the cellular debris, all plates were washed 24 hours after plating. Each plate was gently rocked several times, the media was removed and replaced with 1 ml of 37° C. DMEM. The plate was gently rocked several times, the media was removed and replaced with 500 µl of NeuroBasal medium (Gibco) plus B27 supplements, 2 mM L-glutamine and penicillin and streptomycin. After all plates were washed and refed, N-[4-[(4-fluorophenyl)sulfonyl]phenyl] acetamide, dissolved 2 hydroxypropyl-β-cyclodextrin, was added to cultures at final concentrations ranging from 100 µg/ml to 10 ng/ml. Control wells received 2 hydroxypropyl-β-cyclodextrin only. Using immunostaining protocols described above, 24 well cluster plates were immunostained once per week for up to 10 weeks after treatment with N-[4-[(4-fluorophenyl)sulfonyl]phenyl]acetamide using antibodies against eNCAM, β-tubulin, MAP II, phosphorylated neurofilament or low affinity NGF receptor.

For some experiments, freshly dissociated cortical cells were plated in poly lysine coated T-75 flasks. Cells were fed twice weekly with DMEM+10% FBS. After reaching confluence, cells were removed from the T-75 flask with typsin/EDTA (Gibco), pelleted and media removed. The cell pellet was resuspended in DMEM+10% FBS and split 1 to 5 into new T-75 flasks. This process was repeated 2 more times. After reaching confluence on the fourth passage, cells were removed from the T-75 flask as describe above and plated on poly lysine coated 24 well cluster plates at a density of $1 \times 10^5$ cells per well. Cells were maintained in DMEM+10% FB S until they reached confluence at which point, the media was removed and replaced with NeuralBasal+B27 supplementsN-[4-[(4-fluorophenyl)sulfonyl]phenyl]acetamide was dissolved in 2 hydroxypropyl-β-cyclodextrin and added to cultures at final concentrations ranging from 100 µg/ml to 10 ng/ml. Utilizing the protocol described above, one 24 well cluster plate per week was immunostained using antibodies against either eNCAM, β-tubulin, MAP II, phosphorylated neurofilament or low affinity NGF receptor.

EXAMPLE 3

In Vivo Experiment: Spinal Cord Injury Treatment

Fischer F344 female rats (Taconic, Germantown N.Y.) weighing 175-200 g were subjected to 25 mm weight drop contusion injury as previously described (Gruner J A, *J. Neurotrauma*, 1992 Summer; 9(2):123-8) with slight modifications. Briefly, under isoflurane anethesia, a laminectomy exposing the T8-9 spinal cord segment was performed and a rod weighing 10 g was dropped on the exposed cord from 25 mm height. The rod diameter at its end (where cord-rod interaction takes place) is 2.8 mm. A total of 12 rats were injured. Four animals were used as donor animals, eight as recipients. Two donor animals were administered N-[4-[(4-fluorophenyl)sulfonyl]phenyl]acetamide at a dose of 100 mg/kg orally, and two other animals were treated with vehicle (cyclodextrin, 45% in distilled sterile water). Five days following donor treatment and four weeks following injury, donor animals were euthanized with $CO_2$ according to the Guidelines set by the Panel on Euthanasia of the American Veterinary Medical Association. Bone marrow (BM) cells were harvested from donor animals, and a total of 250,000 cells in a volume of 10 μl (saline vehicle) were injected into the cavity of recipient animals. Two recipient animals received 10 μl saline in the cord cavity, three received BM cells from N-[4-[(4-fluorophenyl)sulfonyl] phenyl]acetamide-treated donors and three from vehicle-treated donors. Four weeks following cell/saline injection, animals were deeply anesthetized using xylazine/ketamine (100 mg and 0.15 mg/kg respectively) and perfused transcardially with ice cold saline followed by 4% paraformaldehyde. Spinal cord tissue was harvested, embedded in paraffin and stained for the Nestin and hematoxylin-eosin/ luxol fast blue. Nestin is a known marker of neural precursor cells (Matthew F. McManus, Li-Chun Chen, Inmaculada Vallejo, and Mario Vallejo; "Astroglial Differentiation of Cortical Precursor Cells Triggered by Activation of the cAMP-Dependent Signaling Pathway," *J. Neurosci.* 1999, 19(20):9004-9015). Control sections lacking the primary antibodies were also processed.

On histological analysis animals treated with bone marrow cells from N-[4-[(4-fluorophenyl)sulfonyl]phenyl]acetamide-treated animals demonstrated a decrease in cavity size at the injury site (approximately half the size) compared with saline treated animals. Doseage levels of with N-[4-[(4-fluorophenyl)sulfonyl]phenyl]acetamide was 100 mg/kg at 20 mg/ml. No difference in cavity size was detected comparing saline treated animals and animals treated with bone marrow cells from vehicle treated donors. A significant increase in cells immunoreactive to nestin above and below the edge of the injury cavity was observed in animals treated with cells from N-[4-[(4-fluorophenyl)sulfonyl]phenyl]acetamide treated donors compared with saline treated or vehicle treated donors.

Cyclodextrin and stains (H&E, Luxol fast blue) were purchased from Sigma-RBI (St. Louis, Mo.).
Xylazine/ketamine was purchased from FarVet St. Paul, Minn.
Paraformaldehyde was purchased from Electron Microscopy Sciences (Ft. Washington Pa.).
Nestin antibody was purchased from: (Developmental Safety Hybridoma Bank, Iowa City, Iowa.).
Secondary horse anti-mouse and the ABC kit were purhased from Vector (Burlingame, Calif.).

Paraffinization was performed as follows:
Spinal cord tissue was harvested from the spinal column and the injury site located. About 1.5 cm piece of the spinal cord tissue at the injury site including 0.5 cm above and below the injury was cut off and placed in a Tissue-Tek uni-cassette (Sakura Finetek U.S.A Inc., Torrance, Calif.) and stored overnight at 4° C. in 0.1 M PBS buffer, pH 7.2. The following day, the PBS was drained off and the uni-cassettes containing the spinal cord was transferred tissue into a basket. The basket was placed in stage 1 of a LEICA TP 1020 automatic paraffin embedding center and the tissue paraffinized according to the following program:

| Stage | Solution | Time minutes |
| --- | --- | --- |
| 1 | 70% Alcohol | 5 |
| 2 | 70% Alcohol | 10 |
| 3 | 95% Alcohol | 15 |
| 4 | 95% Alcohol | 15 |
| 5 | 95% Alcohol | 15 |
| 6 | Absolute Alcohol | 20 |
| 7 | Absolute Alcohol | 20 |
| 8 | Absolute Alcohol | 20 |
| 9 | Xylene | 20 |
| 10 | Xylene | 30 |
| 11 | Paraffin (for infiltration) | 20 |
| 12 | Paraffin (for infiltration) | 20 |

The basket was removed, and the Uni-cassettes containing the dehydrated and infiltrated tissue was transferred into the cassette bath containing molten infiltration paraffin wax at 66° C., in the LEICA EG 1160 paraffin embedding center. The wax bath was covered with the lid attached to the vacuum pump, and the lid pushed onto the cassette bath and the aeration knob shut off to generate vacuum. The vacuum pump was turned on and the tissue infiltrated with paraffin for 45 minutes under vacuum. Five minutes before the infiltration was over, the cold plate was turned on to −5° C. The embedding base molds (15 mm×15 mm×5 mm; Tissue-Tek, Sakura, Torrance, Calif.) were placed in the mold warmer. Each cassette containing the tissue was taken out of the cassette bath and placed onto the warm embedding work area to allow liquid paraffin to drop. The base mold was placed under the dispenser outlet nozzle and filled with embedding liquid paraffin manually, by pushing the paraffin dispenser handle with a pair of forceps. The cassette was opened and the tissue transferred sample onto the mold using warm forceps. The spinal cord tissue was placed longitudinally onto the base mold; but in a vertical position with the grooved bottom part of the cord facing the walls of the base mold. The mold was placed on the cold plate for a moment and the tissue oriented as required, before the wax solidified. After orientation of the specimen, the half-filled mold was re-transferred to the warm plate. The top of the Uni-cassette was removed and the cassette base positioned on top of the mold. The mold was filled up with embedding paraffin. The mold was placed on the cold plate until the wax became entirely solid within a short time. The molds were moved to the farthest end of the cold plate (away from the embedding area) and the wax allowed to solidify for 30 minutes to 1 hour. The molds were stored overnight at −20° C. The following day, the paraffin block containing the tissue was removed from the mold. Sections of 5 μm were mounted on gelatinized slides in a water bath and stained as follows:

Luxol Fast Blue-Hematoxylin & Eosin Staining

The slides were placed on a slide warmer at 45° C. for 15 minutes to adhere tissue to the slides. The slides were transferred into a slide holder and deparaffinized by placing in a 60° C. oven for 20 minutes, allowed to cool for 3 minutes, then further deparaffinized in three washes of xylene, 5 minutes each wash. The tissue was dehydrated in three washes of 100% ethanol and 95% ethanol, 5 minutes each wash. The slide holder was placed staining dish containing a solution of Luxol Fast Blue, and covered. The tissue was stained in Luxol Fast Blue for 2 hours in a 60° C. oven. The staining dish was removed from the oven, placed in a hood, and the cover opened slightly and allowed to cool for 8 minutes. The slide holder was removed from the staining dish containing Luxol Fast Blue and the excess stain blotted out with tissue. The excess stain was removed by placing the slides in 95% ethanol for 5 minutes and then rinsed five times in deionized water, 5 minutes each wash. The sections were differentiated by dipping slides 10 times in Hydroquinone reducing solution followed immediately by five changes through deionized water, 5 minutes each wash. The excess water was blotted out with paper towel and the sections immersed in Harris hematoxylin for 10 minutes. The excess stain was blotted out with paper towel and the sections were rinsed five times in deionized water, 5 minutes each wash. The excess water was blotted out and the sections differentiated by dipping ten times in acid alcohol. The sections were rinsed five times in deionized water, 2 minute each wash. The excess water was blotted out and the sections differentiated by dipping ten times in ammonia water. The sections were rinsed five times, in deionized water, 5 minutes each wash. The sections were immersed in 70% ethanol for two minutes, then in alcohol eosin for 30 seconds. The excess eosin stain was blotted out and the sections differentiated twice by dipping ten times in 95% ethanol. The sections were dehydrated in three washes of absolute ethanol, 5 minutes each wash; cleared twice in methyl salicylate, and thrice in Neo-Clear, 5 minutes each wash. The sections were coverslipped in DPX mounting medium (Electron Microscopy Sciences, Ft. Washington, Pa.). The slides were placed on a hot plate and allowed to dry for 1 hour.

Immunohistochemistry

The slides were placed on a slide warmer for 15 minutes to adhere tissue onto the slides, then transferred into a slide holder and deparaffinized by placing in a 60° C. oven for 20 minutes. The slides were cooled in a hood for 3 minutes then further deparaffinized in three washes of xylene, 3 minutes each wash. The sections were dehydrated in three washes of absolute ethanol, 95% and 70% ethanol; 3 minutes each wash.

Quenching endogenous peroxidate activity: The slides were quenched in a solution containing 0.3% hydrogen peroxide solution, 10% acetone, 10% methanol in 0.1 M PBS for 5 minutes. After this noxious step, the sections were washed twice in PBS; 3 minutes each wash. Each slide was placed into a disposable immunostaining chamber (Shandon, Pittsburg, Pa.), and the chamber in turn placed into an immunostaining chamber holder (Shadon). The sections were washed with 1 ml of 0.1 M PBS-0.4% Triton X-100 buffer for 3 minutes. The sections were incubated for 30 minutes at room temperature in 100 μl of the blocking solution containing 10% normal horse serum (NHS) solution in 0.1 M PBS in 0.4% Triton X-100 buffer.

The sections were incubated overnight at 4° C. with 100 μl of the primary antibody diluted as follows:

| Antibody | Dilution in 10% NHS blocking solution |
|---|---|
| Mouse anti-Nestin | 1:20 |

The sections were washed with 1 ml PBS-Triton X-100 buffer for 3 minutes; then incubated for 1 hour at room temperature with 100 μl of biotinylated secondary antibody, i.e. biotinylated Horse anti-mouse (Vector, Burlingame, Calif.) diluted 1:200 in 10% NHS in 0.1 M PBS-0.4% Triton X-100 buffer. The sections were washed with 1 ml PBS-Triton X-100 buffer for 3 minutes. The sections were incubated for 30 minutes at room temperature with 100 μl of freshly prepared ABC solution (Elite Vectastain ABC kit, Vector Labs) prepared as follows: 1 drop of solution A (ABC kit) was added into 10 ml PBS-TX-100 buffer, mixed well, then 1 drop of solution B (ABC kit) was added to the mixture and mixed well. The solution was allowed to stand for 30 minutes before use. The sections were washed once with 1 ml PBS for 3 minutes, and twice with 1 ml Acetate—Imidazole buffer, 3 minutes each wash.

DAB reaction: The sections were incubated in a reaction mixture prepared as follows: 152 ml of DAB reaction was prepared by dissolving 3.04 g of Nickels ammonium sulfate (Sigma, Saint Louis Mo.) in 154 ml of acetate-imidazole buffer. 30.4 μl of 30% hydrogen peroxide was added to initiate the reaction. Just before dipping the slides, 3.04 ml of 2% DAB reagent was added to the reaction mixture and mixed thoroughly. 14 ml of this reaction mixture was transferred to each slide mailer and the slides dipped. The color of the sections was monitored and the reaction stopped when appropriate (Slides for anti-GFAP and anti-β-Tubulin III were incubated for 4 minutes and the rest for 12 minutes in the DAB reaction). The reaction was stopped by washing the sections three times in PBS, 3 minutes each wash. The sections were dehydrated in three washes of 70%, 95% and absolute ethanol, 3 minutes each; cleared twice in methyl salicylate; and NeoClear, 3 minutes each wash. The sections were coverslipped using DPX mounting medium, and the slides dried on a slide warmer for 1 hour.

EXAMPLE 4

Grown of Neural Cells

Astrocytes: postnatal day 2 (P2) Sprague Dawley rat cortices were aseptically dissected and trypsinized for 20 min at 37° C. in 0.25% trypsin-EDTA (GIBCO) and DNAse (0.2 mg/ml, Worthington). Enzyme action was stopped by the addition of soybean trypsin inhibitor (SIGMA)) and DNAse. Tissue was dissociated into single cell suspension by trituration with a 5 ml pipette, filtered though a 40 μm nylon filter and centrifuged at 500×g for 3 minutes. The pellet was taken up in medium (DMEM/10% fetal bovine serum) and cells were plated into poly-D-lysine (10 μg/ml, SIGMA) T75 flasks (one flask/cortex). After 23 days, astrocytes were trypsinized and replated at a density of 500,000 cells per well into poly-D-lysine-coated 24 well plates. Cultures were grown for an additional 20 days in order to let astrocytes mature. This maturation is known to make the astrocytes less permissive for neurite outgrowth (see G. M. Smith, et al., *Developmental Biology*, 138, 377-390 (1990), and G. M. Smith and J. Silver, *Progress in Brain Research*, Vol. 78, Chapt. 46, D. M. Cash and J. R. Sladek, ed., Elsevier, 1988.

Cortical neurons: mixed cortical cells were dissociated from embryonic day 18 Sprague Dawley rat embryos as described for astrocytes. In order to obtain more pure neuonal cultures, cells were subjected to a differential adhesion by pre-plating them on a non-coated bacterial dish (100 mm diameter) for 1 hour. Non-neuronal cells stick to this plate while neurons stay in the supernatant. Neurons were added to the aged astrocytes at a density of 10,000 cells/well in DEME/10% fetal bovine serum. One day later, the cultures were treated with 1 μg/ml and 10 μg/ml of N-4[4-[(4-fluorophenyl)sulfonyl]phenyl]acetamide. 1 week after treatment, cultures were fixed and immunostained with monoclonal anti-tubulin antibody (SIGMA, 1:800 diluted), followed by rhodamine-conjugated goat-anti-mouse secondary (1:100 dilution). Tubulin labels axons and dentrites.

Analysis: Tubulin-positive cell bodies with a process at least two cell diameters long were counted in 5 visual fields under 10× magnification with a Nikon Eclipse 2000 inverted microscope. Results were expressed as means of quadruplicate wells+/−SEM and are shown in Table I. Any patent application to which this application claims priority is incorporated by reference herein in its entirety.

TABLE I

|  | Number of Neurons | | | | | |
| --- | --- | --- | --- | --- | --- | --- |
|  | Well 1 | Well 2 | Well 3 | Well 4 | mean | +/−SEM |
| control | 93 | 74 | 89 | 74 | 82.50 | 4.97 |
| 1 µg/ml | 132 | 103 | 171 | 176 | 145.50 | 17.25 |
| 10 µg/ml | — | 129 | 173 | 133 | 145.00 | 14.05 |

REFERENCES

Any patent application to which this application claims priority is incorporated by reference herein in its entirety.

While this invention has been described with an emphasis upon preferred embodiments, it will be obvious to those of ordinary skill in the art that variations in the preferred devices and methods can be used and that it is intended that the invention can be practiced otherwise than as specifically described herein. Accordingly, this invention includes all modifications encompassed within the spirit and scope of the invention as defined by the claims that follow.

What is claimed:

1. A method for treating a spinal cord injury in a mammal, comprising administering a population of neuronal stem cells or progenitor cells obtained from bone marrow of a first mammal treated with N-[4-[4-fluorophenyl)sulfonyl]phenyl]acetamide, and delivering the cells to the site of injury in the first mammal or in a second mammal in need thereof to treat said spinal cord injury.

* * * * *